United States Patent
Bachinski et al.

[19]

[11] Patent Number: 6,036,702
[45] Date of Patent: Mar. 14, 2000

[54] MEDICAL GRAFTING CONNECTORS AND FASTENERS

[75] Inventors: Thomas J. Bachinski, Lakeville; David S. Goldsteen, Minneapolis; Daniel J. Sullivan, Medina, all of Minn.

[73] Assignee: Vascular Science Inc., Minneapolis, Minn.

[21] Appl. No.: 08/839,199

[22] Filed: Apr. 23, 1997

[51] Int. Cl.⁷ .................. A61B 17/08; A61F 2/06
[52] U.S. Cl. ................ 606/153; 623/1; 606/198; 606/195
[58] Field of Search .............. 623/1, 12; 606/153, 606/155, 156, 195, 198

[56] References Cited

U.S. PATENT DOCUMENTS

| | | | |
|---|---|---|---|
| 4,214,587 | 7/1980 | Sakura, Jr. | 128/334 |
| 4,503,569 | 3/1985 | Dotter | 3/1.4 |
| 4,592,754 | 6/1986 | Gupte et al. | 623/1 |
| 4,617,932 | 10/1986 | Kornberg | 128/334 R |
| 4,665,906 | 5/1987 | Jervis | 128/92 YN |
| 4,787,899 | 11/1988 | Lazarus | 623/1 |
| 5,104,399 | 4/1992 | Lazarus | 623/1 |
| 5,135,467 | 8/1992 | Citron | 600/16 |
| 5,207,695 | 5/1993 | Trout, III | 623/1 |
| 5,211,658 | 5/1993 | Clouse | 623/1 |
| 5,211,683 | 5/1993 | Maginot | 128/898 |
| 5,275,622 | 1/1994 | Lazarus et al. | 623/1 |
| 5,304,220 | 4/1994 | Maginot | 623/1 |
| 5,316,023 | 5/1994 | Palmaz et al. | 128/898 |
| 5,354,336 | 10/1994 | Kelman et al. | 623/6 |
| 5,387,235 | 2/1995 | Chuter | 623/1 |
| 5,397,345 | 3/1995 | Lazarus | 623/1 |
| 5,397,355 | 3/1995 | Marin et al. | 623/12 |
| 5,443,497 | 8/1995 | Venbrux | 623/1 |
| 5,452,733 | 9/1995 | Sterman et al. | 128/898 |
| 5,456,712 | 10/1995 | Maginot | 623/1 |
| 5,489,295 | 2/1996 | Piplani et al. | 623/1 |
| 5,507,769 | 4/1996 | Marin et al. | 606/198 |
| 5,522,880 | 6/1996 | Barone et al. | 623/1 |
| 5,545,214 | 8/1996 | Stevens | 623/2 |
| 5,676,670 | 10/1997 | Kim | 606/108 |
| 5,695,504 | 12/1997 | Gifford, III et al. | 606/153 |
| 5,843,164 | 12/1998 | Frantzen et al. | 623/1 |
| 5,843,170 | 12/1998 | Ahn | 623/1 |
| 5,843,175 | 12/1998 | Frantzen | 623/1 |

FOREIGN PATENT DOCUMENTS

| | | |
|---|---|---|
| 670 239 | 7/1996 | Australia . |
| 0 539 237 A1 | 4/1993 | European Pat. Off. . |
| 0 637 454 A1 | 2/1995 | European Pat. Off. . |
| 0 680 734 A2 | 11/1995 | European Pat. Off. . |
| 0 684 022 A2 | 11/1995 | European Pat. Off. . |
| 0 701 800 A1 | 3/1996 | European Pat. Off. . |
| 0 712 614 A1 | 5/1996 | European Pat. Off. . |
| 2 269 104 | 2/1994 | United Kingdom . |
| WO 89/08433 | 9/1989 | WIPO . |
| WO 93/00868 | 1/1993 | WIPO . |
| WO 93/20757 | 10/1993 | WIPO . |
| WO 94/01056 | 1/1994 | WIPO . |
| WO 95/21592 | 8/1995 | WIPO . |
| WO 96/14808 | 5/1996 | WIPO . |
| WO 96/18361 | 6/1996 | WIPO . |
| WO 96/22745 | 8/1996 | WIPO . |
| WO 96/25897 | 8/1996 | WIPO . |
| WO 97/13463 | 4/1997 | WIPO . |
| WO 97/13471 | 4/1997 | WIPO . |

*Primary Examiner*—Paul B. Prebilic
*Attorney, Agent, or Firm*—Fish & Neave; Robert R. Jackson

[57] ABSTRACT

A body tissue graft for use in a patient includes a frame structure made of a first elastic material, a covering of a second elastic material on the frame structure, the covering substantially filling openings in the frame structure, and a connector connected to the frame structure. Projections are secured to the connector structure. The projections facilitate attachment of the tubular graft in a patient by securing the graft to the body tissue with which the graft is employed. The connector selectively circumferentially expands and the projections selectively circumferentially expand. This may be done using an inflatable balloon to circumferentially expand the projections. A restraining member may be provided to restrain the projections in a cone shape so that an end of the graft may be used to open an aperture through a side wall of existing body organ tubing and a portion of the projections may enter the aperture.

25 Claims, 22 Drawing Sheets

FIG. 30
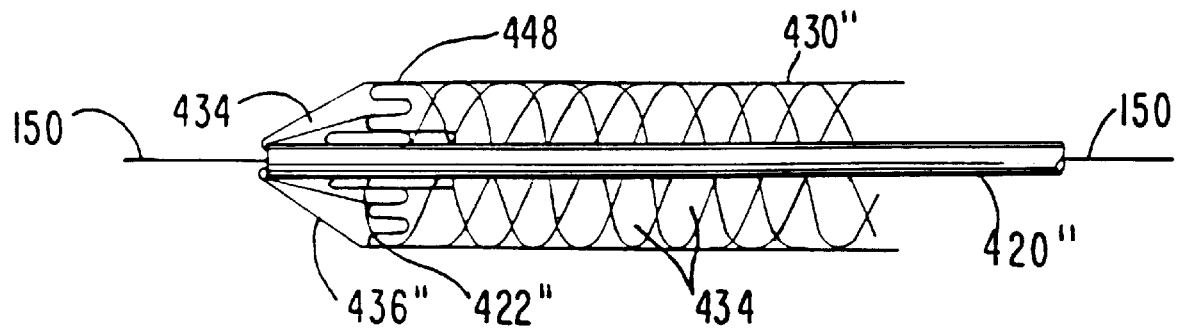
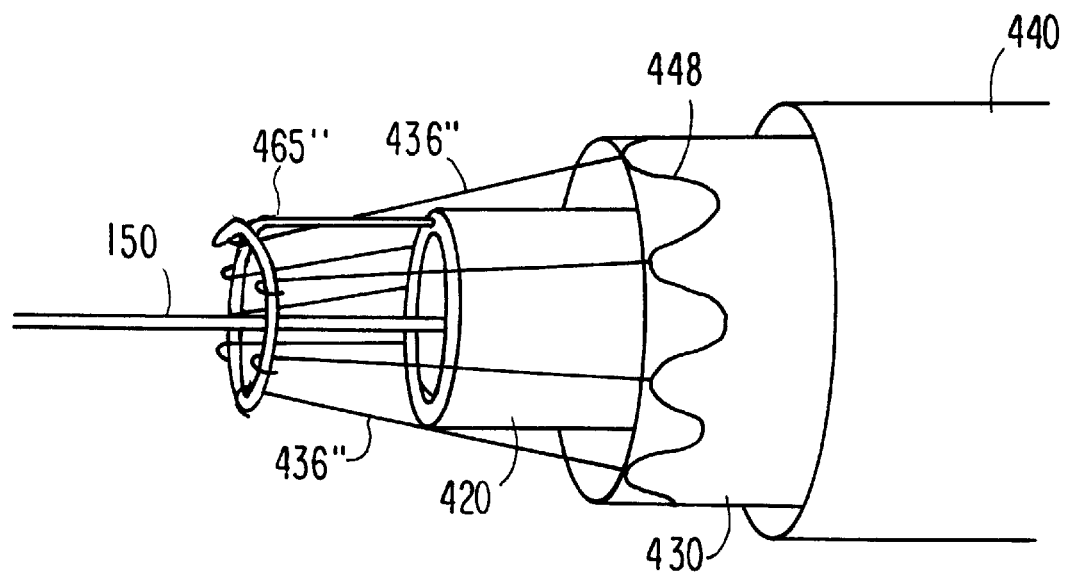
FIG. 32

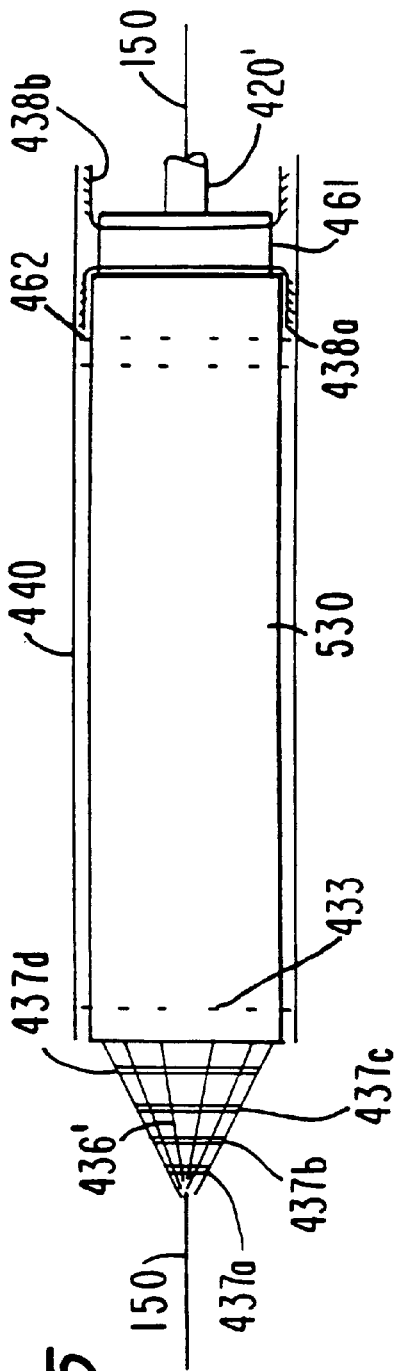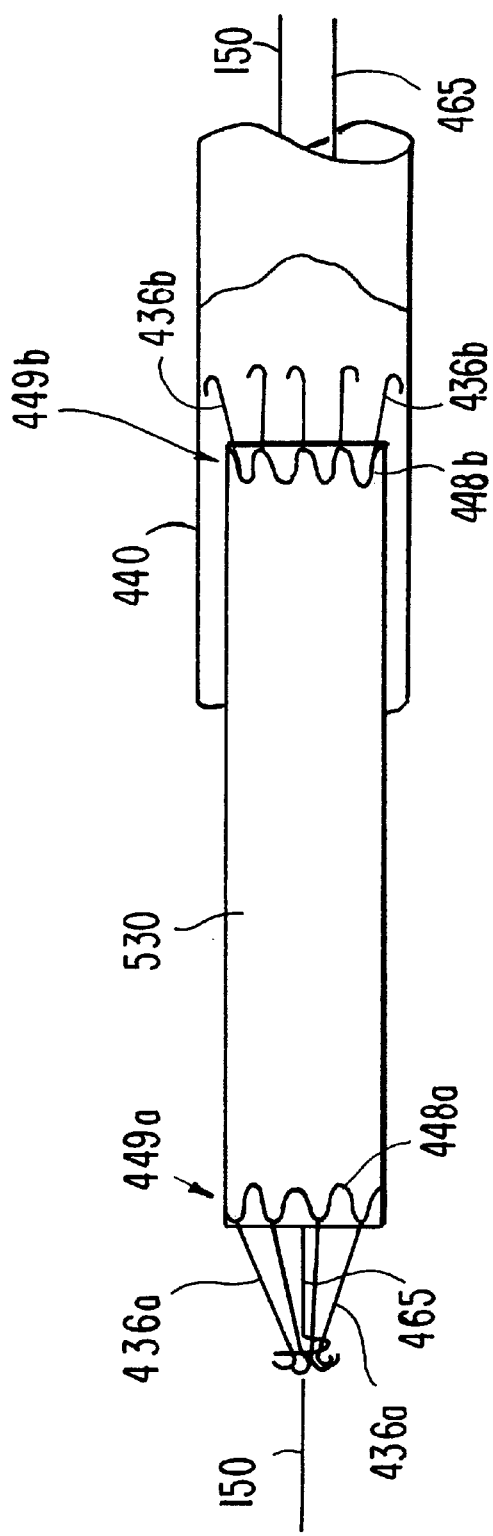

MEDICAL GRAFTING CONNECTORS AND FASTENERS

BACKGROUND OF THE INVENTION

This invention relates to medical grafting methods and apparatus, and more particularly to methods and apparatus for connecting or fastening tubular bypass grafts.

An example of the possible uses of the invention is a minimally invasive cardiac bypass procedure. This example will be considered in detail, but it will be understood that various aspects of the invention have many other possible uses.

Several procedures are known for revascularizing the human heart in order to treat a patient with one or more occluded coronary arteries. The earliest of these procedures to be developed involves exposing the heart by means of a midline sternotomy. Following surgical exposure of the heart, the patient's aorta and vena cava are connected to a heart/lung machine to sustain vital functions during the procedure. The beating of the heart is stopped to facilitate performance of the procedure. Typically, a suitable blood vessel such as a length of the patient's saphenous (leg) vein is harvested for use as a graft. The graft is used to create a new, uninterrupted channel between a blood source, such as the aorta, and the occluded coronary artery or arteries downstream from the arterial occlusion or occlusions. A variation of the above procedure involves relocating a mammary artery of the patient to a coronary artery.

Although the above-described sternotomy procedures are increasingly successful, the high degree of invasiveness of these procedures and the requirement of these procedures for general anesthesia are significant disadvantages. Indeed, these disadvantages preclude use of sternotomy procedures on many patients.

More recently, less invasive procedures have been developed for revascularizing the heart. An example of these procedures is known as thoracostomy, which involves surgical creation of ports in the patient's chest to obtain access to the thoracic cavity. Specially designed instruments are inserted through the ports to allow the surgeon to revascularize the heart without the trauma of a midline sternotomy. Drugs may be administered to the patient to slow the heart during the procedure. Some thoracostomy procedures involve relocating a mammary artery to a coronary artery to provide a bypass around an occlusion in the coronary artery.

Thoracostomy bypass procedures are less traumatic than sternotomy bypass procedures, but they are still too traumatic for some patients. Also, the number of required bypasses may exceed the number of mammary arteries, thereby rendering thoracostomy procedures inadequate to fully treat many patients.

Another technique for revascularizing the human heart involves gaining access to the thoracic cavity by making incisions between the patient's ribs. This procedure is known as thoracotomy. It is also substantially less traumatic than midline sternotomy, but it is still too traumatic for some patients.

In view of the foregoing, even less traumatic approaches have been developed for revascularizing a patient, as described in Goldsteen et al. U.S. patent application Ser. No. 08/745,618, filed Nov. 7, 1996, and hereby incorporated by reference herein in its entirety. With such approaches, a graft (e.g., of saphenous vein) can be delivered to an operative site in the patient through the patient's existing arteries and veins. The graft is typically inserted between two attachment sites in the patient's existing body organs (e.g., between a site along the patient's aorta and a site along the coronary artery downstream from a coronary artery occlusion).

Thus the above-mentioned Goldsteen et al. reference shows, among other things, methods and apparatus for installing tubular bypass grafts intralumenally. The Goldsteen et al. reference shows methods and apparatus in which each end of the graft site is approached separately and intralumenally, penetrated, and then a longitudinal structure (e.g., element 150 in the Goldsteen et al. reference) is established between the ends of the graft site. This longitudinal structure may extend intralumenally all the way out of the patient's body from both ends of the graft site. The graft is fed into the patient's body intralumenally along the longitudinal structure until it is in the desired position extending from one end of the graft site to the other. Each end of the graft is then secured at a respective end of the graft site and the longitudinal structure is withdrawn from the patient.

Tubular artificial grafts are needed in various medical procedures. For example, such grafts may be needed to replace diseased or damaged sections of natural tubular body tissue such as in the circulatory system, the urinary tract, etc. Or such grafts may be needed to make new connections in natural tubular body tissue systems such as bypass or shunt connections in the circulatory system. In general, an artificial tubular graft may be needed as either a temporary or permanent installation.

Important considerations regarding the use of artificial grafts include ease of use, time required for installation, secureness of installation, and performance after installation. Improvements are constantly sought in all of these areas.

It is therefore an object of this invention to provide improved grafts.

It is therefore a further object of this invention to provide improved methods and apparatus for the connection of grafts, whether natural or artificial.

It is therefore a further object of the invention to provide improved graft structures for use in the repair, replacement, or supplementing of natural body organ structures or tissues, and to provide methods and apparatus for fastening or connecting such graft structures.

It is therefore a further object of this invention to provide improved methods and apparatus for installing medical grafts, whether natural or artificial.

SUMMARY OF THE INVENTION

This and other objects of the invention are accomplished in accordance with the principles of the invention by providing apparatus for use as a body tissue graft and methods for securing the graft in a patient comprising a frame structure made of a first elastic material, a covering of a second elastic material on the frame structure, the covering substantially filling openings in the frame structure, and a connector connected to the frame structure. Projections are secured to the connector structure. The projections facilitate attachment of the tubular graft in a patient by securing the graft to the body tissue with which the graft is employed. The connector selectively circumferentially expands and the projections selectively circumferentially expand. This may be done using an inflatable balloon to circumferentially expand the projections and the connector. A restraining member may be provided to restrain the projections in a cone shape so that an end of the graft may be used to open an aperture through a side wall of existing body organ tubing and a portion of the projections may enter the aperture. The connector structures of this invention may be used with artificial grafts having any construction (i.e., other than the frame-and-covering construction mentioned above), and they may also be used with natural body tissue grafts.

Further features of the invention, its nature, and various advantages will be more apparent from the accompanying drawings and the following detailed description of the preferred embodiments.

BRIEF DESCRIPTION OF THE DRAWINGS

FIG. 26b is a simplified elevational view of an illustrative embodiment of one component of the apparatus shown in FIG. 26a.

FIG. 30 is a simplified longitudinal sectional view showing another possible alternative construction of portions of the apparatus shown in FIG. 7.

FIG. 32 is a simplified longitudinal sectional view showing still another possible alternative construction of portions of the apparatus shown in FIG. 7.

FIG. 34b is an elevational view taken from the right in FIG. 34a.

FIG. 35 is a simplified elevational view of apparatus which can be used as an alternative to certain apparatus components shown in FIG. 7.

FIG. 36 is a view similar to a composite of FIGS. 7 and 9 showing another alternative illustrative embodiment of certain aspects of the invention.

DETAILED DESCRIPTION OF THE PREFERRED EMBODIMENTS

Because the present invention has a number of different applications, each of which may warrant some modifications of such parameters as instrument size and shape, it is believed best to describe certain aspects of the invention with reference to relatively generic schematic drawings. To keep the discussion from becoming too abstract, however, and as an aid to better comprehension and appreciation of the invention, references will frequently be made to specific uses of the invention. Most often these references will be to use of the invention to provide a bypass around an occlusion or obstruction (generically referred to as a narrowing) in a patient's coronary artery, and in particular a bypass from the aorta to a point along the coronary artery which is downstream from the coronary artery narrowing. It is emphasized again, however, that this is only one of many possible applications of the invention.

Figure 1:
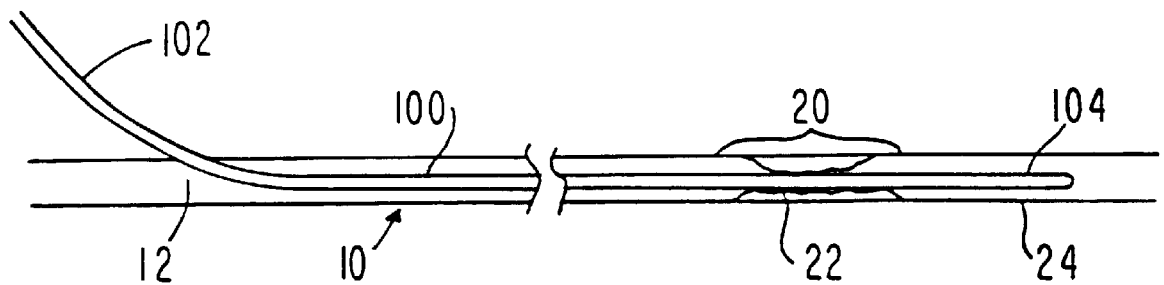
FIG. 1 is a simplified longitudinal sectional view showing a portion of an illustrative procedure and related apparatus in accordance with this invention.

Assuming that the invention is to be used to provide a bypass from the aorta around a coronary artery narrowing, the procedure may begin by inserting an elongated instrument into the patient's circulatory system so that a distal portion of the instrument extends through the coronary artery narrowing to the vicinity of the point along the artery at which it is desired to make the bypass connection. This is illustrated by FIG. 1, which shows elongated instrument 100 entering the patient's circulatory system 10 at a remote location 12 and passing coaxially along vessels in the circulatory system until its distal end portion 104 passes through narrowing 22 in coronary artery 20 and reaches the downstream portion 24 of the artery to which it is desired to make a bypass connection. For example, the entry location 12 of instrument 100 may be a femoral (leg) artery of the patient, a brachial artery of the patient, or any other suitable entry point. It will be appreciated, however, that entry point 12 is typically remote from the location at which the bypass is to be provided, and that control of instrument 100 throughout its use is from the proximal portion 102 that is outside the patient at all times.

Figure 2:
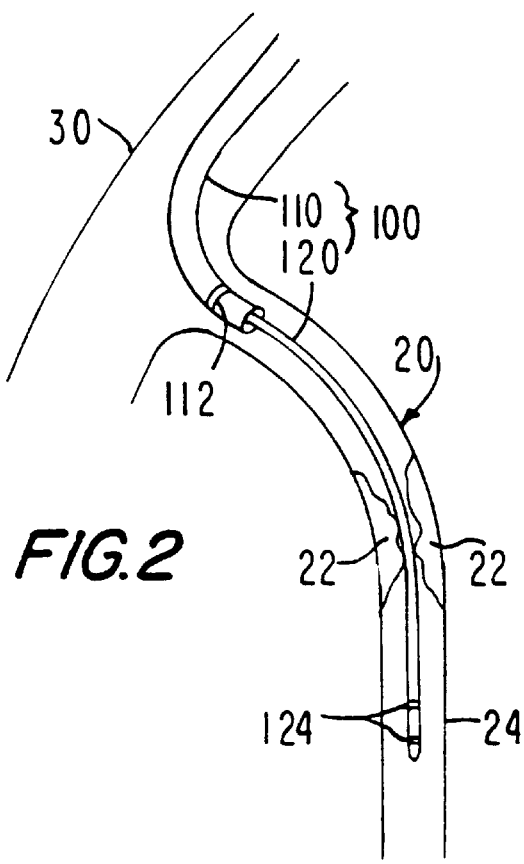
FIG. 2 is a simplified longitudinal sectional view showing a portion of a more particular illustrative procedure and related apparatus in accordance with the invention.

For the illustrative procedure being discussed, FIG. 2 shows a preferred embodiment of instrument 100 in more detail. As shown in FIG. 2, instrument 100 may include a catheter tube 110 which is inserted (from location 12 in FIG. 1) via the patient's aorta 30 to the ostium of coronary artery 20. Another tubular structure 120 is then extended from the distal end of catheter 110, through narrowing 22 to location 24.

Figure 3:
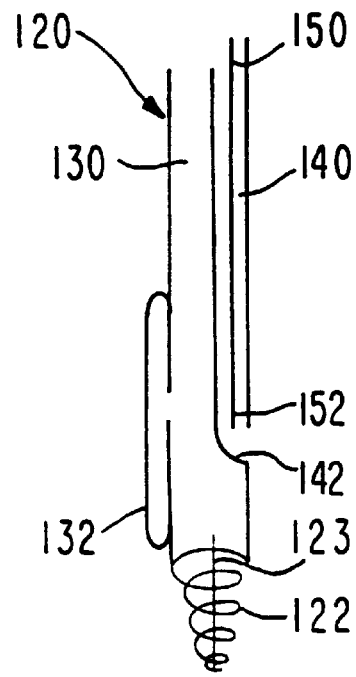
FIG. 3 is a simplified longitudinal sectional view showing an illustrative embodiment of a portion of the FIG. 2 apparatus in more detail.

An illustrative construction of tubular structure 120 is shown in more detail in FIG. 3. There it will be seen that structure 120 may have two lumens 130 and 140. Near the distal end of structure 120, lumen 130 communicates with the interior of an inflatable balloon 132 on one side of structure 120, while lumen 140 opens out to the opposite side of structure 120. Lumen 140 contains a longitudinal structure 150 which may be a stylet wire with a sharpened distal tip 152. Structure 120 may be provided with a distal spring tip 122 to help guide the distal end of structure 120 along coronary artery 20 and through narrowing 22. A safety ribbon 123 (e.g., of the same material as tip 122) may be connected at its proximal end to the distal end of member 120 and at its distal end to the distal end of tip 122 to improve the performance of tip 122 and to help prevent separation of any portion of tip 122 from structure 120 in the event of damage to tip 122. Structure 120 may have radiologic (e.g., radio-opaque or fluoroscopically viewable) markers 124 at suitable locations to help the physician place the structure where desired in the patient's body. Catheter 110 may also have radiologic markers 112 for similar use. Balloon 132 is initially deflated. Longitudinal structure 150 is initially retracted within lumen 140. However, the distal portion of lumen 140 is shaped (as indicated at 142 in FIG. 2) to help guide the distal tip 152 of structure 150 out to the side of structure 120 when structure 150 is pushed distally relative to structure 120. This is discussed in more detail below. As earlier description suggests, each of components 110, 120, and 150 is separately controllable from outside the patient, generally indicated as region 102 in FIG. 1.

Figure 4:
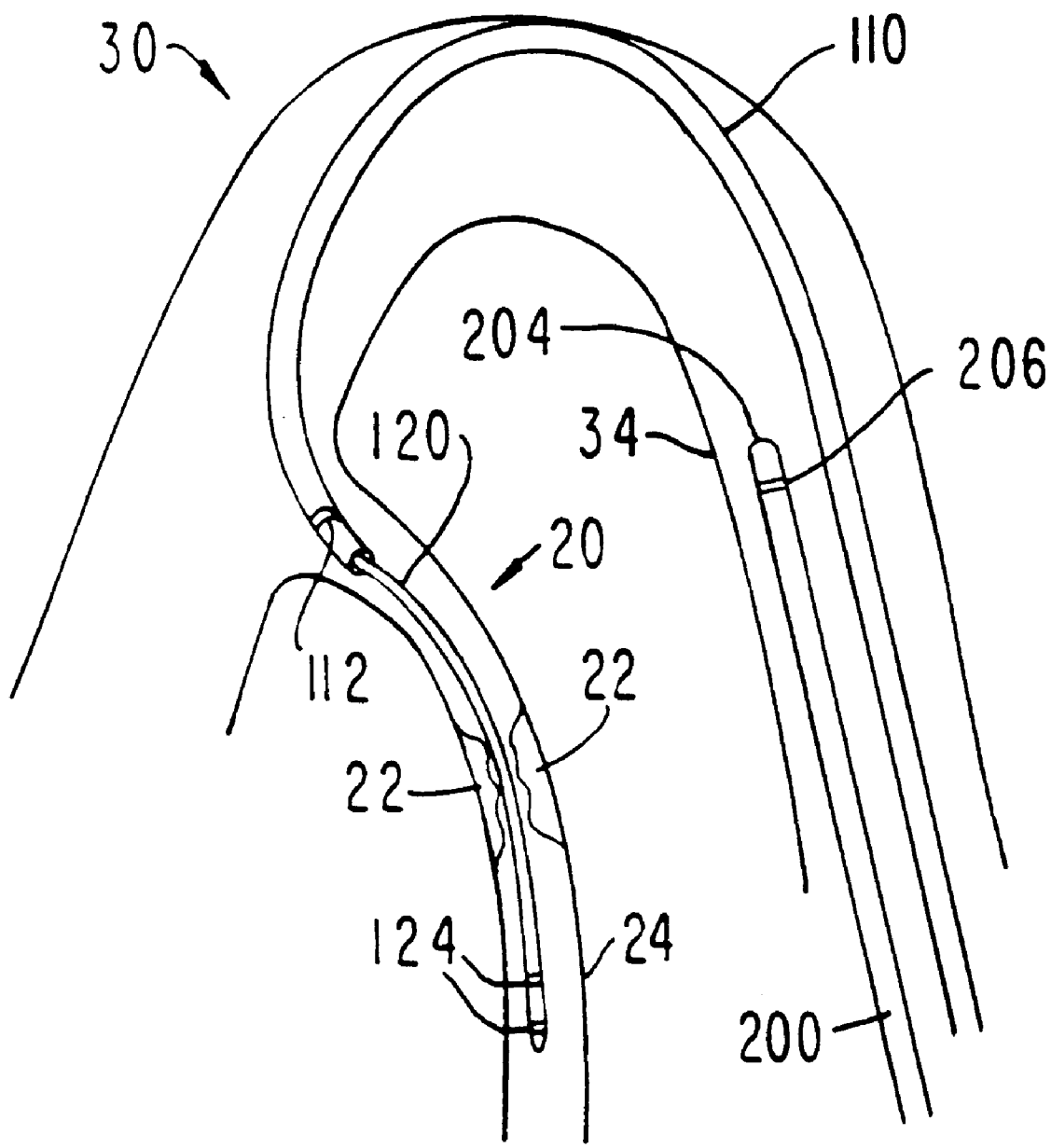
FIG. 4 is a view similar to FIG. 2 showing a later stage in the illustrative procedure depicted in part by FIG. 2, together with related apparatus, all in accordance with this invention.

After instrument 100 is positioned as shown in FIGS. 1 and 2, a second elongated instrument 200 is similarly introduced into the patient's circulatory system 10. For example, instrument 200 may enter the patient via a femoral artery, a brachial artery, or any other suitable location, which again is typically remote from the bypass site. If one femoral artery is used to receive instrument 100, the other femoral artery may be used to receive instrument 200. Or the same femoral artery may be used to receive both instruments. Or any other combination of entry points may be used for the two instruments. Instrument 200 is inserted until its distal end is adjacent to the point 34 in the circulatory system which it is desired to connect to point 24 via a bypass. This is illustrated in FIG. 4 where the distal end of instrument 200 is shown at location 34 in aorta 30. The particular location 34 chosen in FIG. 4 is only illustrative, and any other location along aorta 30 may be selected instead. Radiologic markers 206 may be provided on the distal portion of instrument 200 to help the physician position the instrument where desired. Note that FIG. 4 shows portions of instruments 100 and 200 side by side in aorta 30.

The next step in the illustrative procedure being described is preferably to deploy a snare loop 354 (FIG. 5) from the distal end 204 of instrument 200 through the aorta wall to a location outside the coronary artery wall adjacent coronary artery portion 24. This is explained in more detail in the above-mentioned Goldsteen et al. reference. (Alternatively, this step could be performed somewhat later.) Then stylet wire 150 is moved in the distal direction so that its distal tip 152 passes through the wall of the coronary artery. As was mentioned earlier, the distal end of the stylet wire lumen in tube 120 is shaped to help guide stylet wire 150 through the coronary artery wall.

Figure 5:
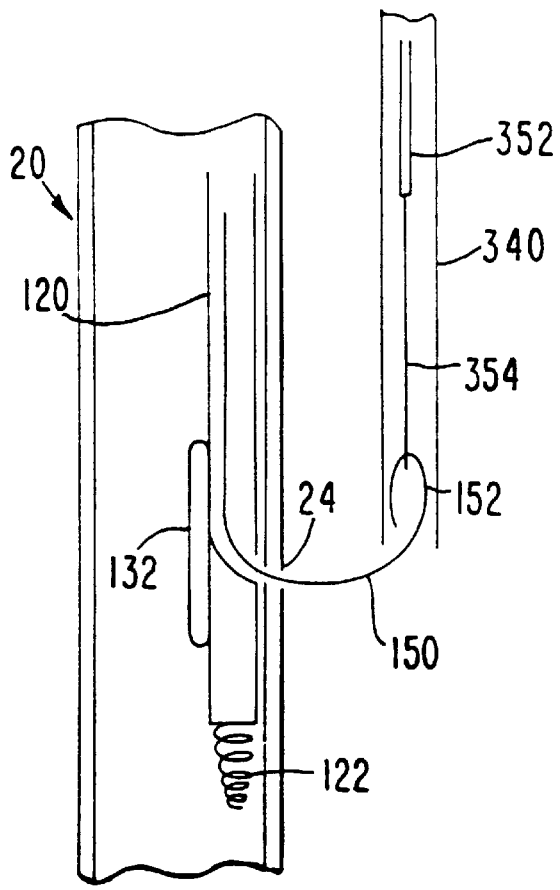
FIG. 5 shows an even later stage in the illustrative procedure depicted in part by FIG. 4, together with related apparatus, all in accordance with this invention.

Once wire 150 is through snare loop 354, snare sheath or lumen 340 is moved distally relative to the snare loop as shown in FIG. 5. This causes snare loop 354 to close down on wire 150. Snare sheath or lumen 340 also tends to trap the distal portion of wire 150 and to fold that wire portion back on itself inside sheath or lumen 340. The longitudinal structures 150 and 350 are securely interengaged inside snare sheath or lumen 340. The next step is to pull snare wire 352 in the proximal direction all the way out of the patient. Because of the interengagement between wires 150 and 352, withdrawing wire 352 pulls as much additional wire 150 into the patient from external location 102 (FIG. 1). When wire 352 has been completely removed from the patient, there is then one continuous wire 150 from outside the patient at 102, through the patient, to outside the patient again. Wire 150 can now be moved in either longitudinal direction through the patient. This wire or another wire could be used to help pull various apparatus into the patient via the tube or tubes through which the wire passes.

Figure 6:
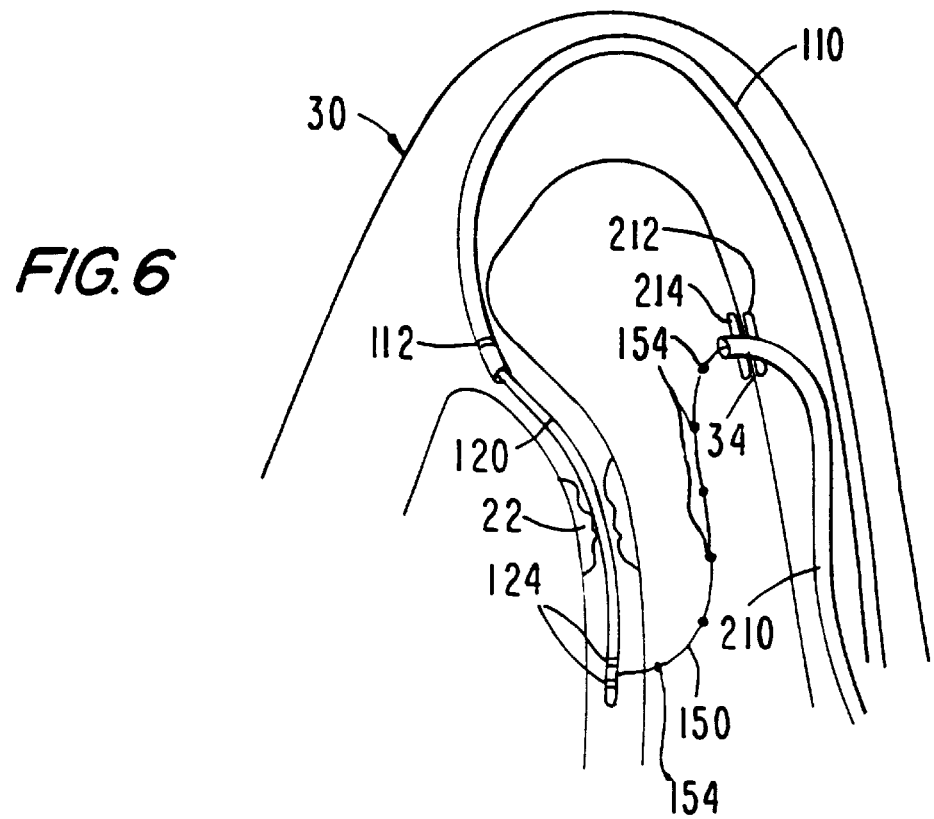
FIG. 6 is a view similar to FIG. 4 showing a still later stage in the illustrative procedure depicted in part by FIG. 5.

After one continuous wire 150 has been established through the patient as described above, the other snare components such as 340 may be withdrawn from the patient by pulling them proximally out of catheter 210. The condition of the apparatus inside the patient is now as shown in FIG. 6. Note that the presence of fixed outlets for the wire from the distal portion of tube 120 and the distal end of catheter 210 prevents wire 150 from cutting tissues 20 and 30 when the wire is pulled in either longitudinal direction. The portion of wire 150 extending through the interior of the patient between elements 120 and 210 may have radiologic markers 154 equally spaced along its length. These can be viewed radiologically by the physician to determine the distance between regions 24 and 34 via wire 150. This helps the physician select the correct length of graft needed between regions 24 and 34.

The next phase of the illustrative procedure being described is to install a new length of tubing or graft between regions 24 and 34. The new length of tubing may be either an artificial graft, natural body organ tubing harvested from the patient's body, or a combination of artificial and natural tubing (e.g., natural tubing coaxially inside artificial tubing). In the following discussion it is assumed that the new tubing is to be natural tubing (e.g., a length of the patient's saphenous vein that has been harvested for this purpose) inside an artificial conduit. When such a combination of natural and artificial conduits is used, both conduits can be delivered and installed simultaneously, or the outer artificial conduit can be delivered and installed first, and then the inner natural conduit can be delivered and installed. The following discussion initially assumes that the latter technique is employed.

Figure 8:
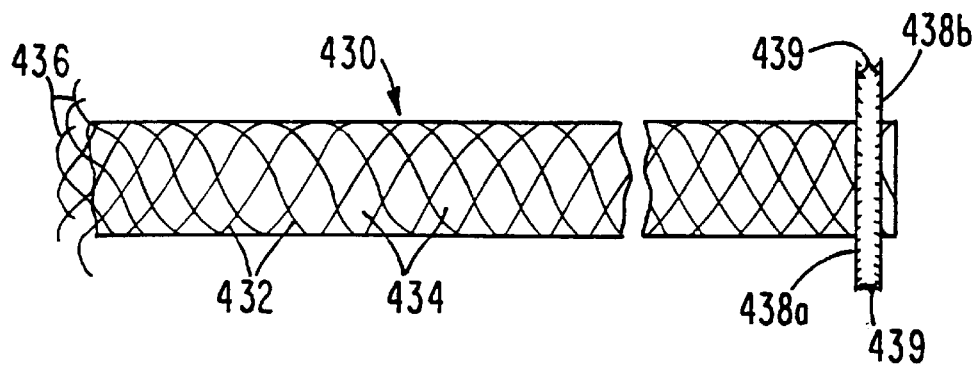
FIG. 8 is a simplified elevational view of an illustrative embodiment of one component of the FIG. 7 apparatus.

An illustrative embodiment of an artificial graft 430 is shown in FIG. 8. Although any suitable construction can be used for the main portion of graft 430, a particularly preferred construction is shown and described in the above-mentioned Goldsteen et al. reference. For example, this graft construction may include a tubular mesh framework 432 of nitinol covered with silicone 434 to substantially fill in the interstices in the framework. Additional details, features, and alternatives regarding this type of graft construction will be found in the above-mentioned Goldsteen et al. reference, and in Bachinski et al. U.S. patent application Ser. No. 08/839,080, filed Apr. 23, 1997, which is also hereby incorporated by reference herein in its entirety. Grafts having this type of construction are extremely elastic and they can be radically deformed without damage or permanent change in shape. For example, a graft of this construction can be stretched to a small fraction of its original diameter, and it thereafter returns by itself to its original size and shape without damage or permanent deformation of any kind. Grafts of this type can be made with any desired porosity (e.g., through the silicone). For use in the circulatory system, they can also be made so that they pulse in response to pressure pulses in the blood flowing through them, very much like the pulsation of natural blood vessels. This can be important to discouraging the formation of clots in the graft.

Figure 7:
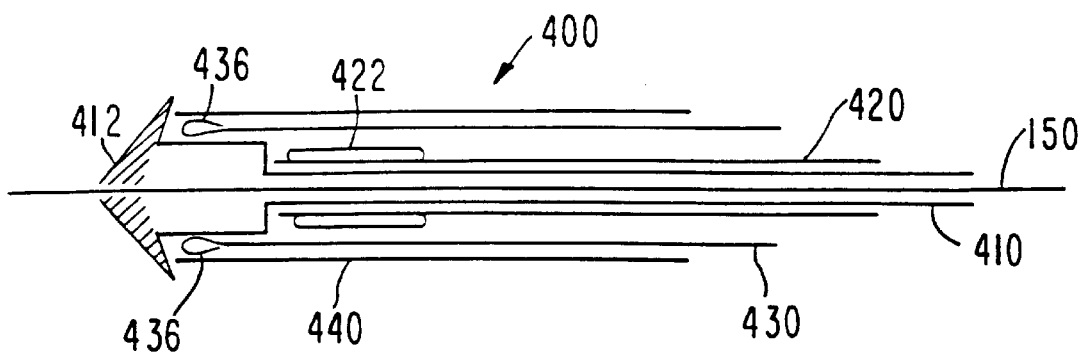
FIG. 7 is a simplified longitudinal sectional view of an illustrative embodiment of a portion of an illustrative apparatus in accordance with this invention.

In accordance with the above-stated assumptions, the next step in the procedure is to use catheter 210 and wire 150 to deliver an artificial conduit such as graft 430 so that it extends between regions 24 and 34. The distal portion of an illustrative assembly 400 for doing this is shown in FIG. 7. As shown in FIG. 7 assembly 400 includes a threaded, conical, distal tip 412 mounted on a tubular member 410 (e.g., metal hypotube) through which wire 150 can freely pass. It should be mentioned here that in this embodiment tip 412 is selectively collapsible to facilitate its withdrawal from the patient after it has served its purpose. Another tubular member 420 is disposed concentrically around tubular member 410. An inflatable balloon 422 is mounted on the distal end of tubular member 420. Tubular member 420 includes an axially extending lumen (not shown in FIG. 7) for use in selectively inflating and deflating balloon 422. Balloon 422 is shown deflated in FIG. 7.

Coaxially around tubular member 420 is artificial graft conduit 430. As has been mentioned, an illustrative embodiment of a suitable graft conduit 430 is shown in FIG. 8 and includes a tube formed of a frame 432 of a first highly elastic material (such as nitinol) with a covering 434 of a second highly elastic material (e.g., a rubber-like material such as silicone) substantially filling the apertures in the frame. At its distal end, extensions of frame 432 are flared out to form resilient struts 436. The struts 436 may have hooks and/or barbs disposed thereon. Near the proximal end of conduit 430 two axially spaced resilient flaps 438a and 438b with prongs 439 are provided.

In assembly 400 (see again FIG. 7, and also FIG. 9), struts 436 and flaps 438 are compressed radially inwardly and confined within conduit delivery tube 440, which coaxially surrounds conduit 430. Indeed, conduit 430 may be somewhat circumferentially compressed by tube 440.

Figure 9:
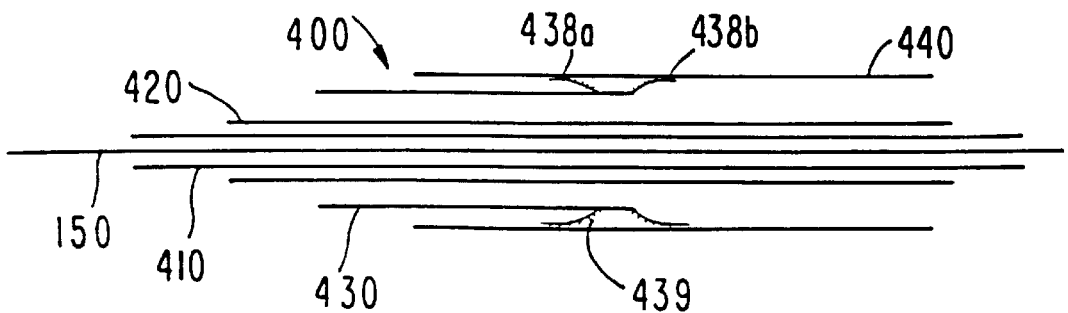
FIG. 9 is a simplified longitudinal sectional view of an illustrative embodiment of another portion of the FIG. 7 apparatus.

The portion of assembly 440 at which the proximal end of conduit 430 is located is shown in FIG. 9. There it will be seen how flaps 438 are confined within conduit delivery tube 440. FIG. 9 also shows how tubes 410, 420, and 440 extend proximally (to the right as viewed in FIG. 9) from the proximal end of conduit 430 so that the physician can remotely control the distal portion of assembly 400 from outside the patient.

Figure 10:
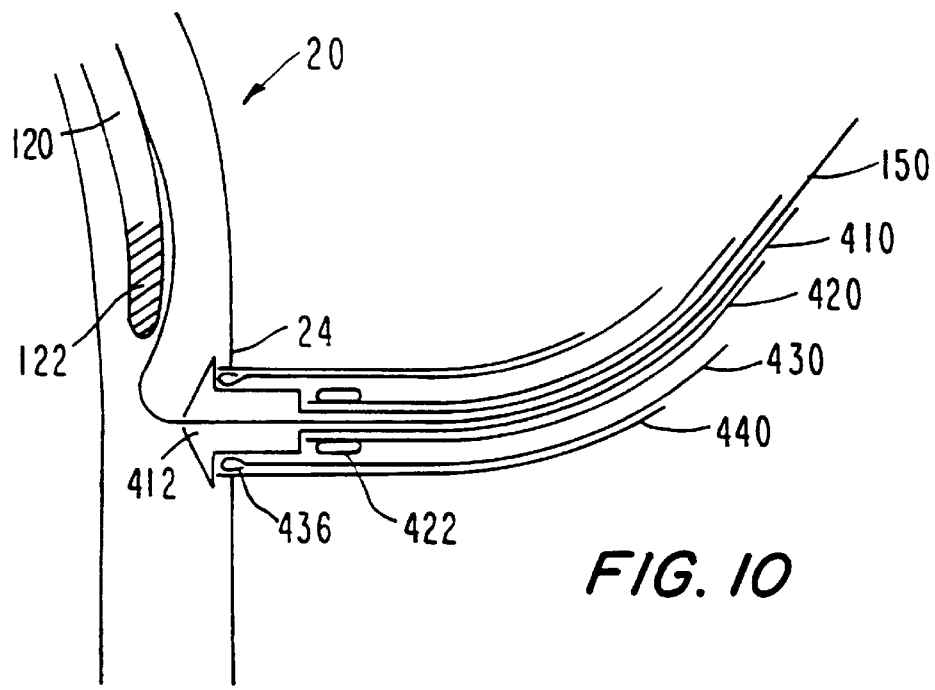
FIG. 10 is a view similar to a portion of FIG. 6 showing an even later stage in the illustrative procedure depicted in part by FIG. 6.

To install artificial graft conduit 430 in the patient between regions 24 and 34, assembly 400 is fed into the patient along wire 150 through catheter 210. When tip 412 reaches coronary artery portion 24, tip 412 is threaded into and through the coronary artery wall by rotating tube 410 and therefore tip 412. (Tube 120 may be pulled back slightly at this time to make sure that it does not obstruct tip 412.) The passage of tip 412 through the coronary artery wall opens up the aperture in that wall. After tip 412 passes through the artery wall, that wall seals itself against the outside of the distal portion of conduit delivery tube 440 as shown in FIG. 10.

Figure 11:
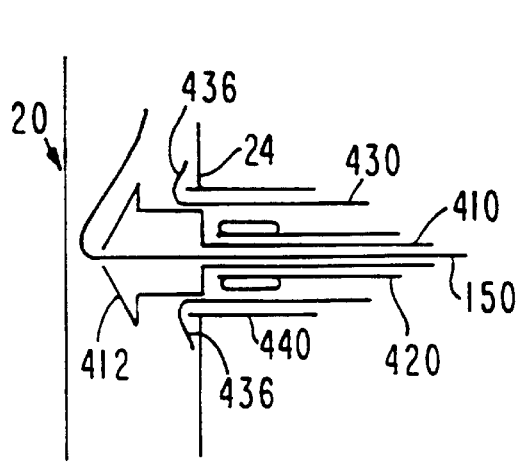
FIG. 11 is a view similar to FIG. 10 showing a still later stage in the FIG. 10 procedure.

The next step is to push tube 410 and tip 412 distally relative to delivery tube 440, which is held stationary. Conduit 430 is initially moved distally with components 410 and 412. This may be done by inflating balloon 422 so that it engages conduit 430, and then moving tube 420 distally with components 410 and 412. Distal motion of conduit 430 moves struts 436 beyond the distal end of delivery tube 440, thereby allowing the struts 436 to spring out inside coronary artery 20 as shown in FIG. 11. This prevents the distal end of conduit 430 from being pulled proximally out of the coronary artery. If balloon 422 was inflated during this phase of the procedure, it may be deflated before beginning the next phase.

Figure 12:
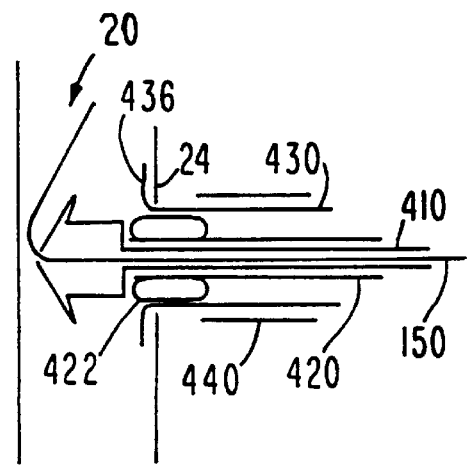
FIG. 12 is a view similar to FIG. 11 showing an even later stage in the FIG. 11 procedure.

The next step is to pull delivery tube 440 back slightly so that it is withdrawn from coronary artery 20. Then tube 420 is moved distally so that balloon 422 is radially inside the annulus of struts 436. Balloon 442 is then inflated to ensure that struts 436 (and barbs and/or hooks if provided) are firmly set in coronary artery 20. Conditions are now as shown in FIG. 12. Cross sections of balloon 422 may be L-shaped when inflated (one leg of the L extending parallel to the longitudinal axis of conduit 430, and the other leg of the L extending radially outward from that longitudinal axis immediately distal of struts 436). This may further help to ensure that struts 436 fully engage the wall of coronary artery 20.

Figure 13:
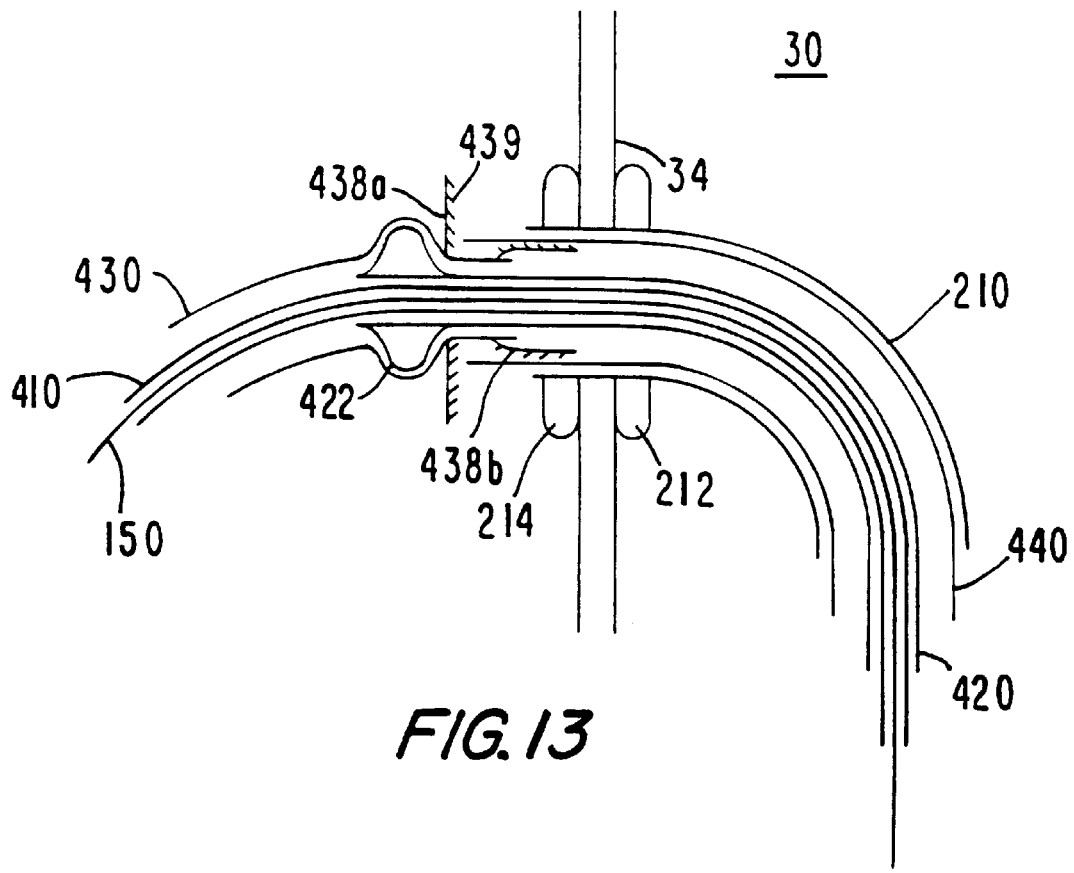
FIG. 13 is a view similar to another portion of FIG. 6 showing a still later stage in the FIG. 12 procedure.

The next step is to deflate balloon 422. Then delivery tube 440 is withdrawn proximally until flap 438a (but not flap 438b) is distal of the distal end of the delivery tube. This allows flap 438a to spring radially out as shown in FIG. 13. Tube 420 is then withdrawn until balloon 422 is just distal of flap 438a. Then balloon 422 is inflated, producing the condition shown in FIG. 13.

Figure 14:
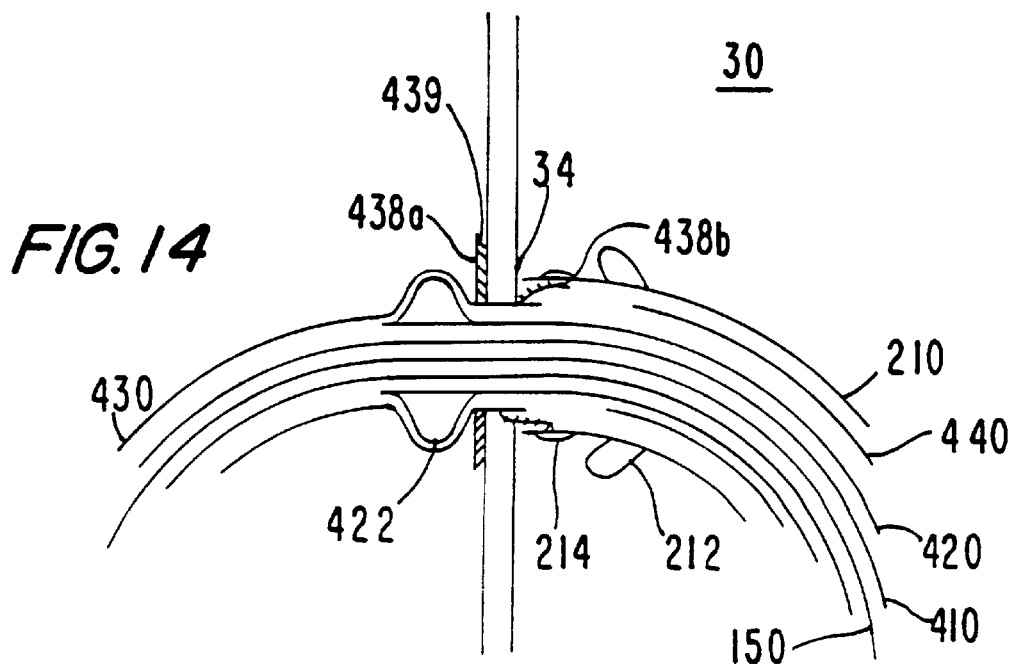
FIG. 14 is a view similar to FIG. 13 showing an even later stage in the FIG. 13 procedure.

The next steps are (1) to deflate distal balloon 214, (2) to proximally withdraw catheter 210 a short way, (3) to proximally withdraw tube 420 to press flap 438a against the outer surface of the aorta wall, and (4) to proximally withdraw delivery tube 440 by the amount required to allow flap 438b to spring out against the interior of catheter 210, all as shown in FIG. 14. As a result of the above-described proximal withdrawal of tube 420, the prongs 439 on flap 438a are urged to enter the aorta wall tissue to help maintain engagement between flap 438a and the wall of the aorta. Inflated balloon 422 helps to set prongs 439 in the tissue when tube 420 is tugged proximally.

Figure 14A:
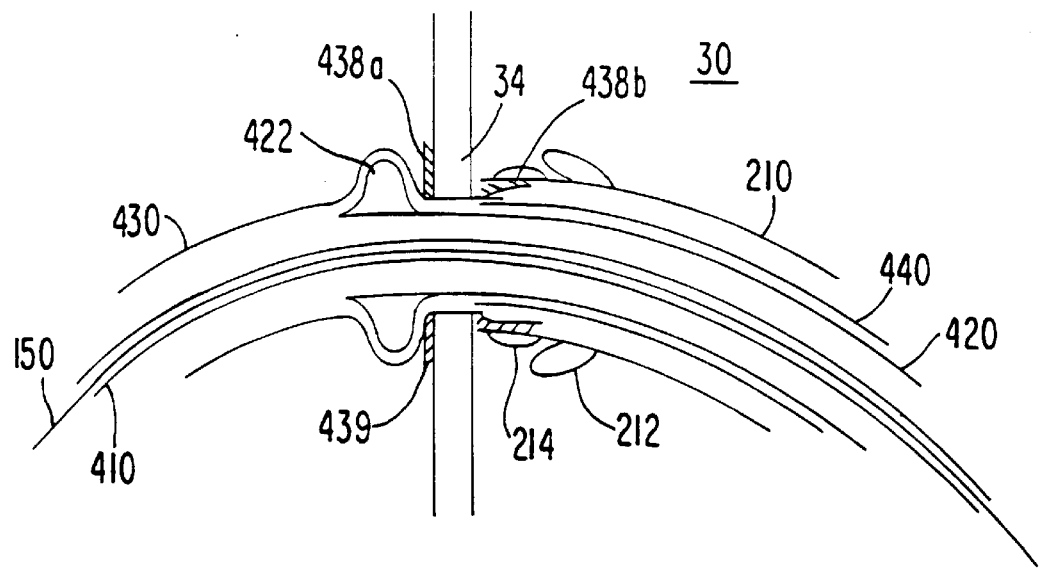
FIG. 14a is a view similar to FIG. 14 showing a still later stage in the FIG. 14 procedure.

The next step is to insert the distal portion of delivery tube 440 into the proximal end of conduit 430 as shown in FIG. 14a. The distal end of conduit 430 may be inserted all the way to the proximal end of balloon 422 (see FIG. 15 for a depiction of this). A purpose of this step is to subsequently help control the rate at which blood is allowed to begin to flow through conduit 430.

Figure 14B:
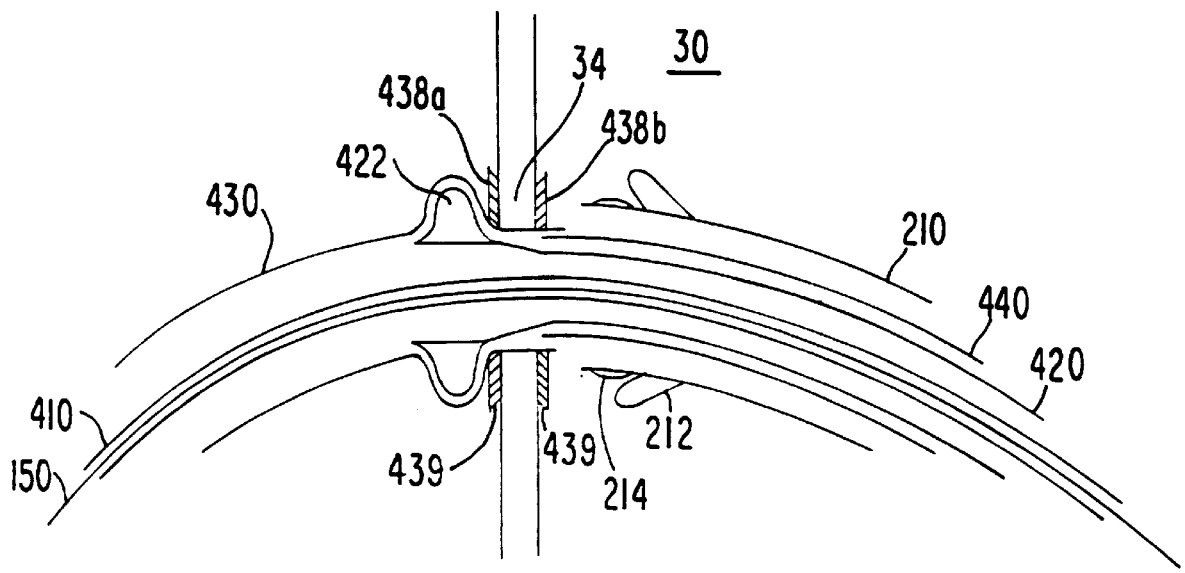
FIG. 14b is a view similar to FIG. 14a showing an even later stage in the FIG. 14a procedure.
Figure 15:
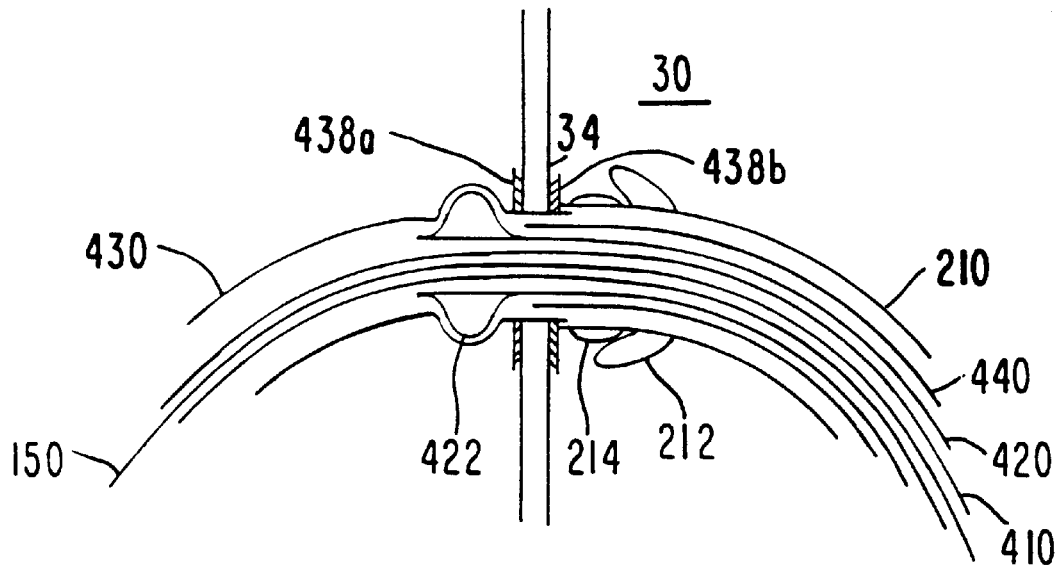
FIG. 15 is a view similar to FIG. 14b showing a still later stage in the FIG. 14b procedure.

The next step is to proximally withdraw catheter 210 by the amount required to release flap 438b to spring out against the interior of the wall of aorta 30 as shown in FIG. 14b. Catheter 210 may be subsequently pushed back against flap 438b as shown in FIG. 15 to help securely engage that flap against the aorta wall.

Figure 16:
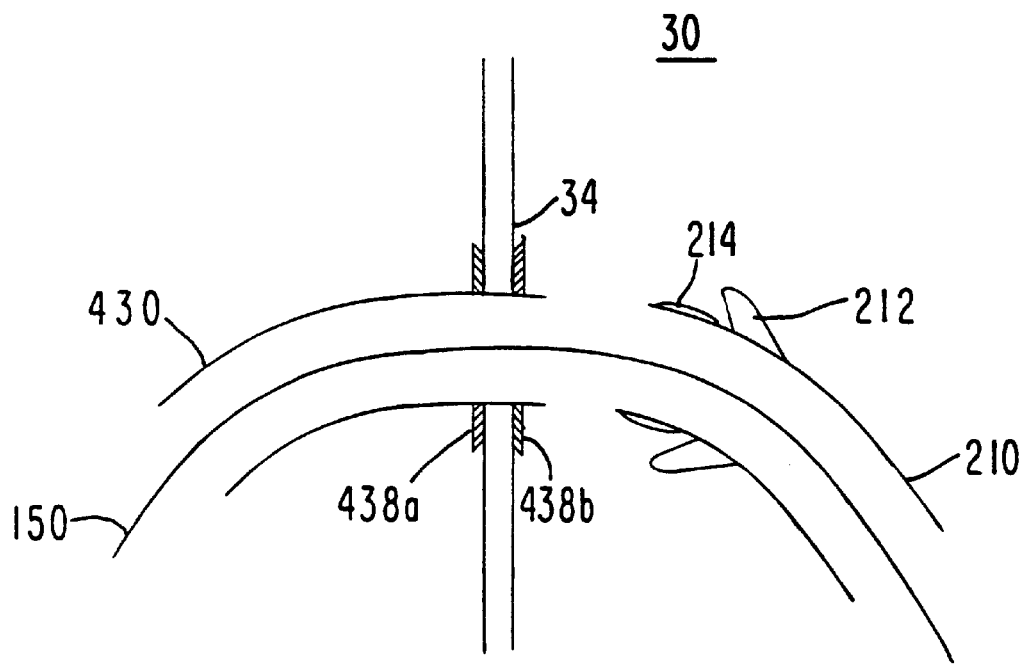
FIG. 16 is a view similar to FIG. 15 showing an even later stage in the FIG. 15 procedure.

Artificial graft conduit 430 is now fully established between aorta region 34 and coronary artery region 24. The next steps are therefore to deflate balloon 422 and proximally withdraw tube 420, to collapse tip 412 and proximally withdraw tube 410, and to proximally withdraw delivery tube 440. The proximal end of conduit 430 is now as shown in FIG. 16. As possible alternatives to what is shown in FIG. 16, the distal end of catheter 210 could be left pressed up against proximal flap 438b and/or the distal portion of delivery tube 440 could be left inside the proximal portion of conduit 430. If the latter possibility is employed, then delivery of the natural graft conduit (described below) can be through tube 440.

As has been mentioned, the illustrative procedure being described assumes that natural body conduit (e.g. a length of the patient's saphenous vein that has been harvested for this purpose) is installed inside artificial conduit 430 after installation of the latter conduit. An illustrative assembly 500 for delivering a length of natural body conduit to installed conduit 430 is shown in FIG. 17.

Figure 17:
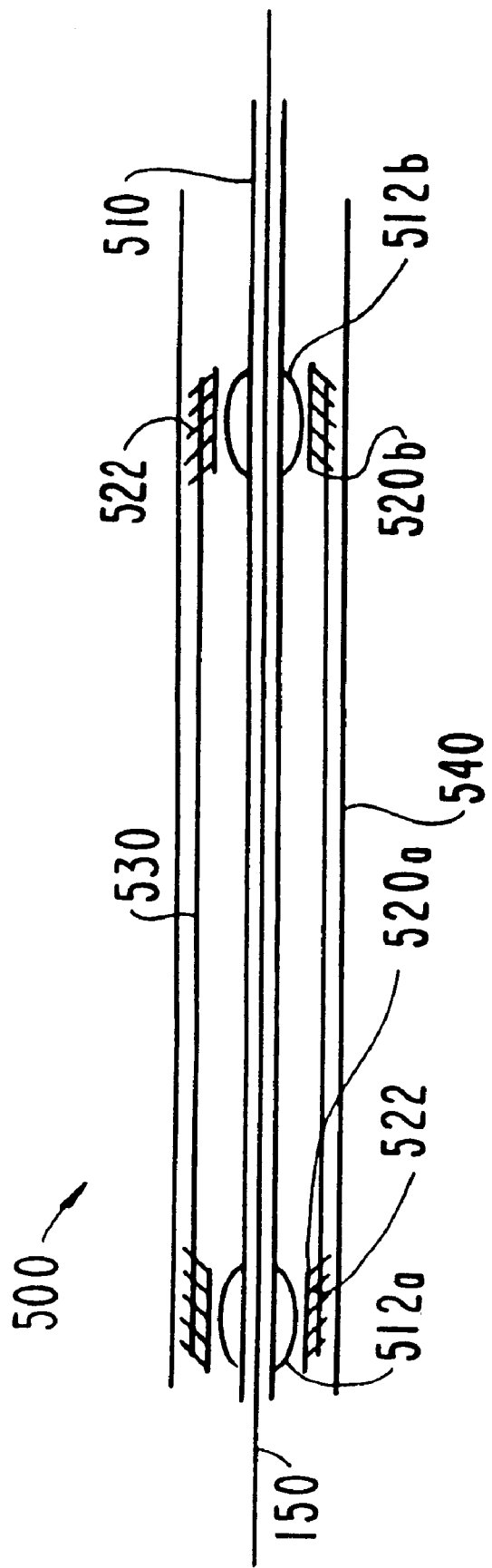
FIG. 17 is a simplified longitudinal sectional view of an illustrative embodiment of a portion of more apparatus in accordance with this invention.

As shown in FIG. 17, assembly 500 includes a tube 510 disposed around wire 150 so that tube 510 is freely movable in either direction along wire 150. Tube 510 has an inflatable annular balloon 512a near its distal end and another inflatable annular balloon 512b spaced in the proximal direction from balloon 512a. Tube 510 includes separate inflation lumens (not shown) for each of balloons 512 so that the balloons can be separately inflated and deflated. An annular collar structure or ring 520a is disposed concentrically around balloon 512a, and a similar annular collar structure or ring 520b is disposed concentrically around balloon 512b. Balloons 512 may be partly inflated. Each of rings 520 may have radially outwardly extending prongs 522. The rings 520 may alternatively or additionally be fluted or provided with raised portions (alternatives that are discussed below (e.g., in connection with FIGS. 27–29a and 36)). A length of natural body conduit 530 (e.g., saphenous vein as mentioned earlier) extends from ring 520a to ring 520b around the intervening portion of tube 510. Prongs 522 may extend through the portions of conduit 530 that axially overlap rings 520. A delivery tube 540 is disposed around conduit 530. In use, tubes 510 and 540 extend proximally (to the right as viewed in FIG. 17) out of the patient to permit the physician to remotely control the distal portion of assembly 500.

Instead of prongs 522, the rings 520 may be provided with fluted or raised structures that grip the graft conduit 430. Instead of balloons 512 being both on the same tube 510, balloon 512a may be on a relatively small first tube, while balloon 512b is on a larger second tube that concentrically surrounds the proximal portion of the first tube. The first and second tubes are axially movable relative to one another, thereby allowing the distance between balloons 512 to be adjusted for grafts 530 of different lengths. An illustrative apparatus of this kind is shown in Goldsteen et al. U.S. patent application Ser. No. 08/839298, filed Apr. 17, 1997, which is hereby incorporated by reference herein.

Figure 18:
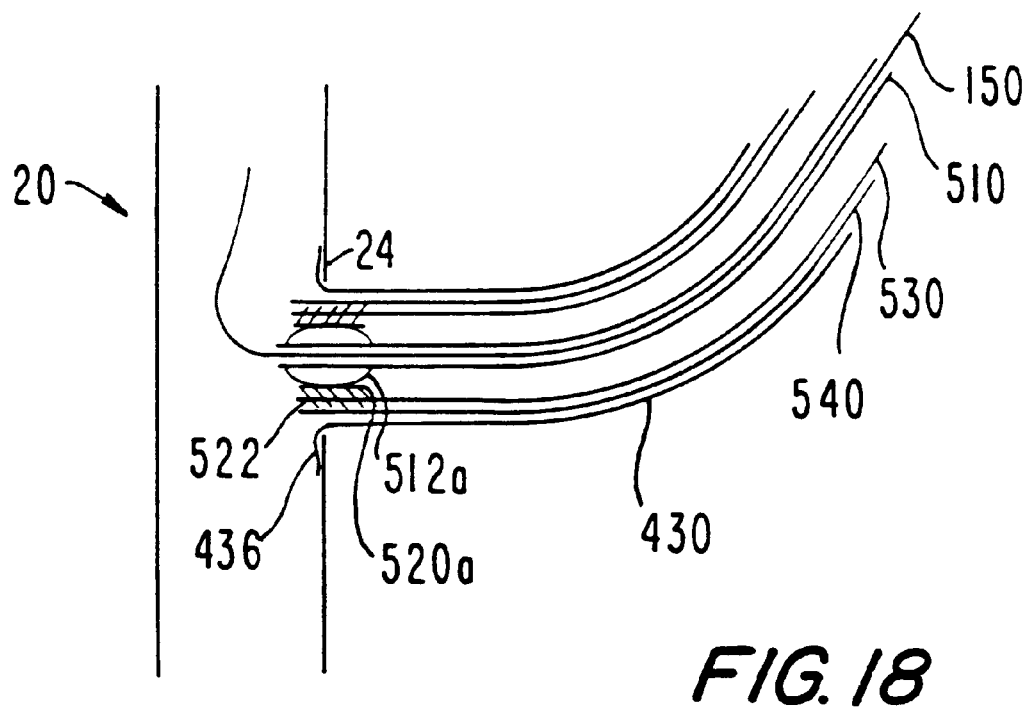
FIG. 18 is a view similar to FIG. 12 showing a later stage in the FIG. 16 procedure.
Figure 20:
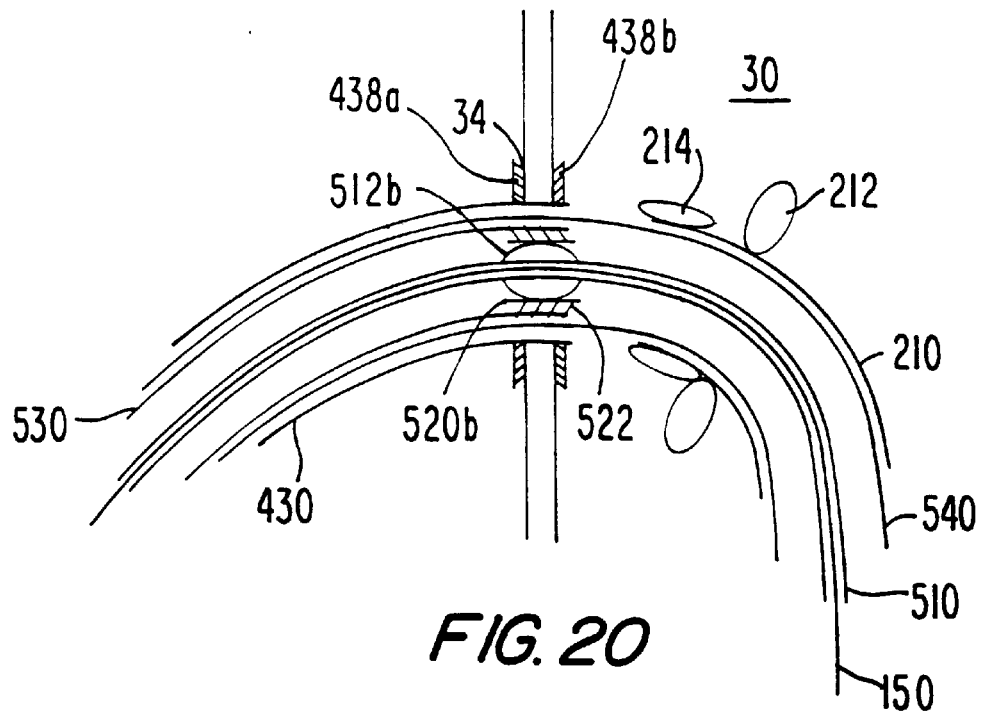
FIG. 20 is a view similar to FIG. 16 showing an even later stage in the FIG. 19 procedure.

Assembly 500 is employed by placing it on wire 150 leading into catheter 210. Assembly 500 is then advanced distally along wire 150 through catheter 210 and then into conduit 430 until the distal end of conduit 530 is adjacent the distal end of conduit 430 and the proximal end of conduit 530 is adjacent the proximal end of conduit 430. The condition of the apparatus at the distal end of assembly 500 is now as shown in FIG. 18. The condition of the apparatus at the proximal end of conduit 530 is as shown in FIG. 20.

Figure 19:
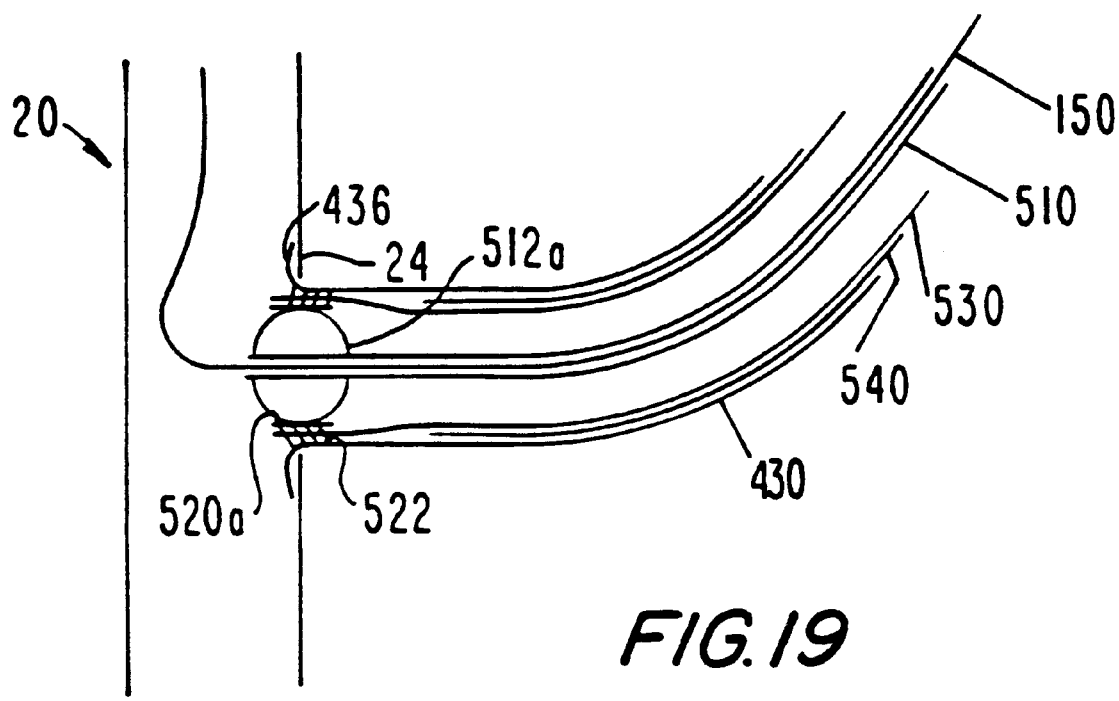
FIG. 19 is a view similar to FIG. 18 showing a still later stage in the FIG. 18 procedure.

The next step is to proximally withdraw delivery tube 540 so that the distal portion of conduit 530 and distal ring 520a are no longer inside the distal portion of delivery tube 540. Then distal balloon 512a is inflated to circumferentially expand ring 520a and to set prongs 522 through conduit 530 into the surrounding portion of conduit 430 and coronary artery wall portion 24. This provides a completed anastomosis of the distal end of conduit 530 to coronary artery 20. FIG. 19 shows the condition of the apparatus at this stage in the procedure.

Figure 21:
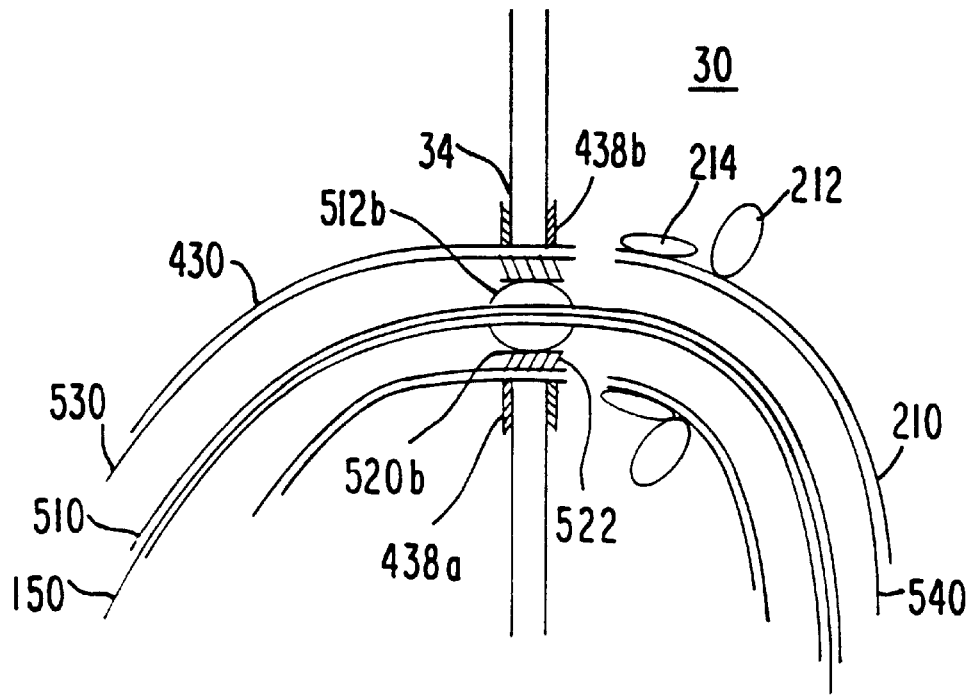
FIG. 21 is a view similar to FIG. 20 showing a still later stage in the FIG. 20 procedure.
Figure 22:
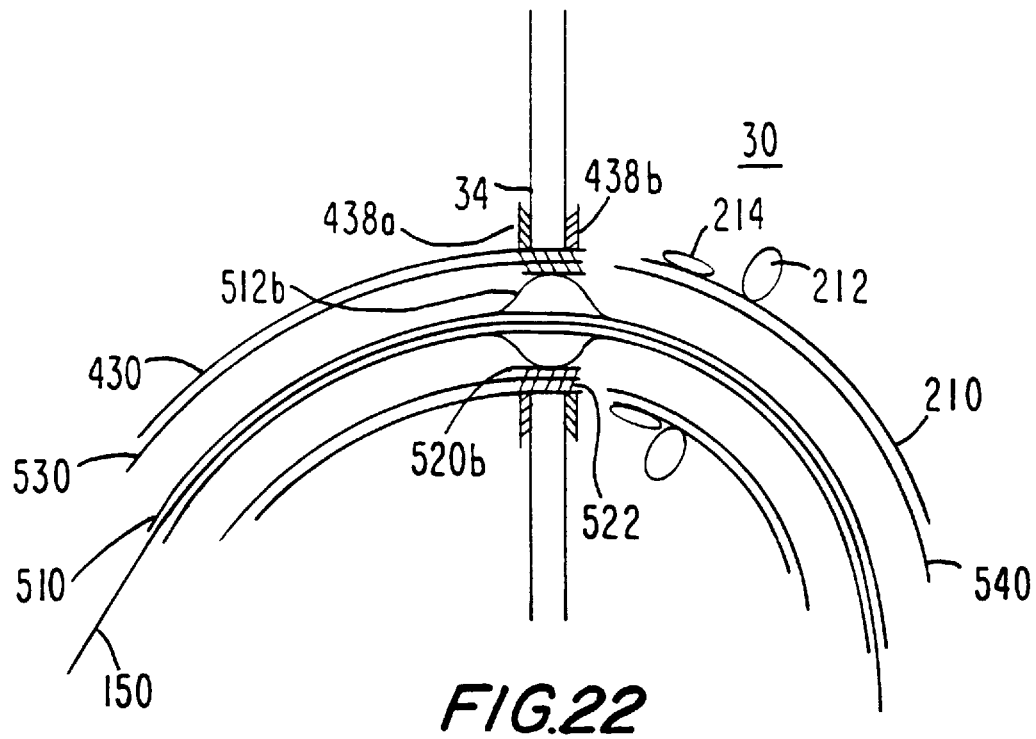
FIG. 22 is a view similar to FIG. 21 showing an even later stage in the FIG. 21 procedure.

The next step is to continue to proximally withdraw delivery tube 540 until the proximal end of conduit 530 and proximal ring 520b are no longer inside tube 540 (see FIG. 21). Then proximal balloon 512b is inflated to circumferentially expand ring 520b and thereby set prongs 522 through conduit 530 into the surrounding portion of conduit 430 and aorta wall portion 34 (see FIG. 22). This provides a completed anastomosis of the proximal end of conduit 530 to aorta 30.

Figure 23:
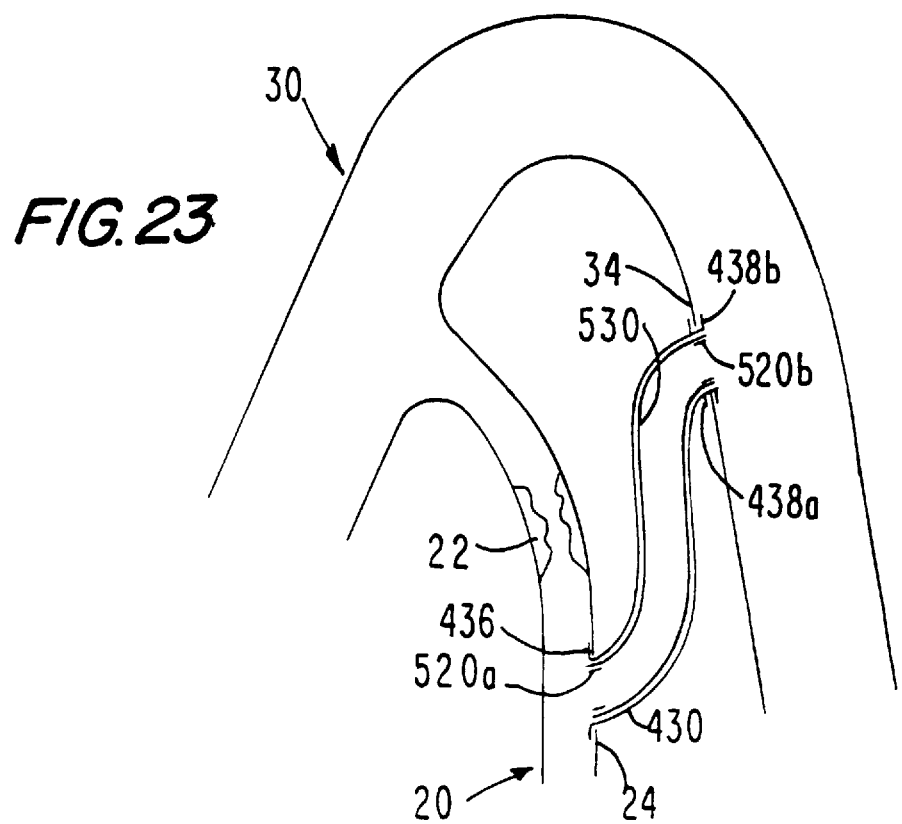
FIG. 23 is a view similar to FIG. 6 showing the end result of the procedure depicted in part by FIG. 22.

The next step is to deflate balloons 512a and 512b and proximally withdraw tube 510 and delivery tube 540 from the patient via catheter 210. Then wire 150 is withdrawn from the patient, either by pulling it proximally from catheter 210 or by pulling it proximally from elements 110 and 120. Lastly, elements 110, 120, and 210 are all proximally withdrawn from the patient to conclude the procedure. The bypass that is left in the patient is as shown in FIG. 23. This bypass extends from aorta 30 at location 34 to coronary artery 20 at location 24. The bypass includes natural body conduit 530 inside artificial graft conduit 430. One end of the bypass is anchored and anastomosed to coronary artery 20 by prongs 436 and ring 520a. The other end of the bypass is anchored and anastomosed to aorta 30 by flaps 438 and ring 520b.

Figure 24:
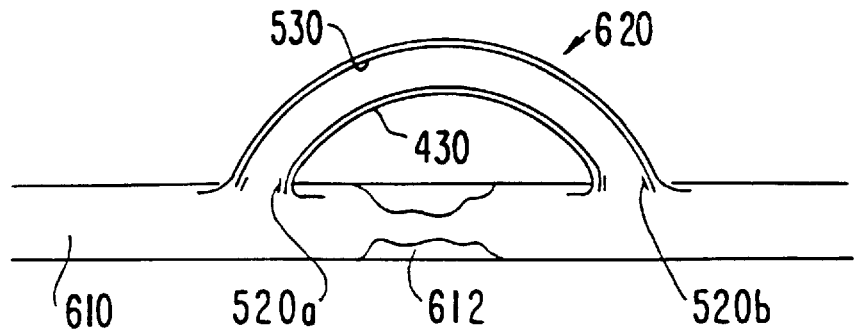
FIG. 24 is a simplified longitudinal sectional view showing an end result similar to FIG. 23 but in a different context.

The particular uses of the invention that have been described in detail above are only illustrative of many possible uses of the invention. Other examples include same-vessel bypasses in the coronary area and vessel-to-vessel and same-vessel bypasses in other portions of the circulatory system (including neurological areas, renal areas, urological areas, gynecological areas, and peripheral areas generally). A same-vessel bypass is a bypass that extends from one portion of a vessel to another axially spaced portion of the same vessel. In FIG. 24, bypass 620 is a same-vessel bypass around a narrowing 612 in vessel 610. For ease of comparison to previously described embodiments, the various components of bypass 620 are identified using the same reference numbers that are used for similar elements in FIG. 23. The invention is also applicable to procedures similar to any of those mentioned above, but for non-circulatory systems such as urological tubing.

Figure 25:
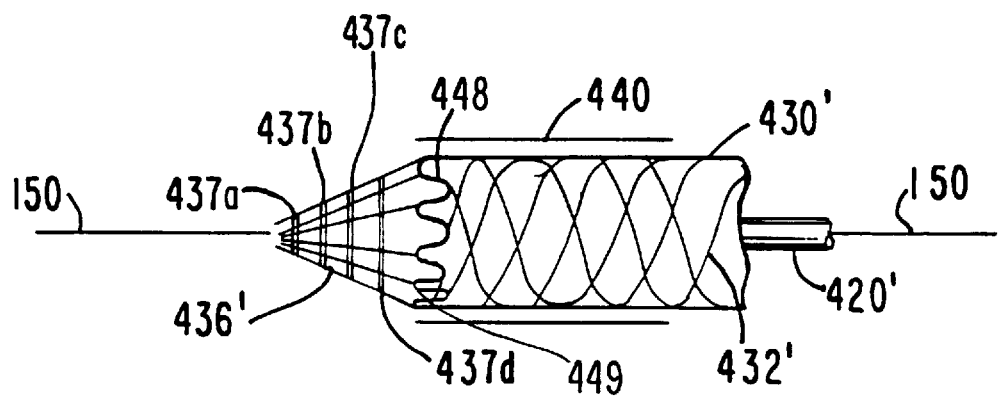
FIG. 25 is a simplified elevational view (partly in section) showing another possible alternative construction of portions of the FIG. 7 apparatus.
Figure 26:
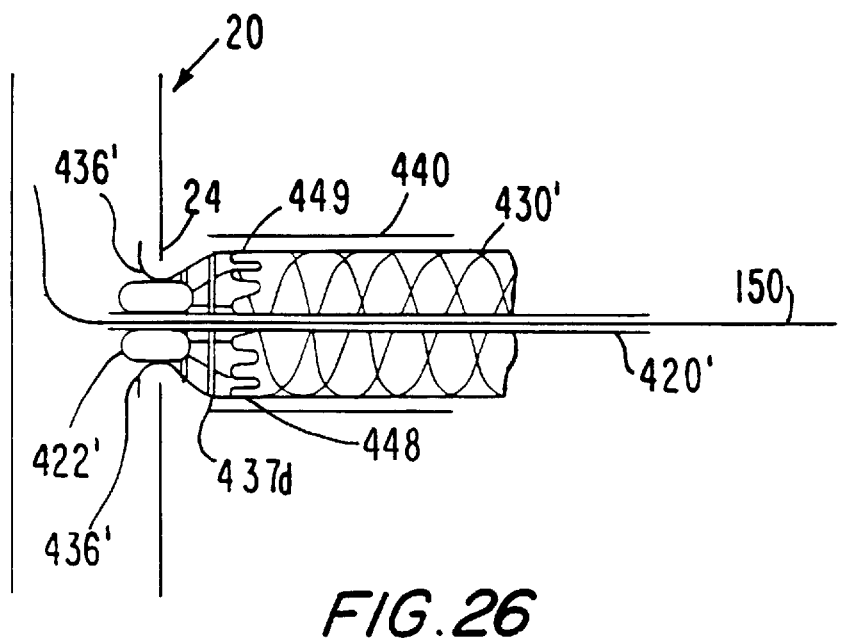
FIG. 26 is a simplified longitudinal sectional view of the FIG. 25 apparatus in another operating condition.

Another illustrative alternative embodiment of some of the instrumentation shown in FIG. 7 is shown in FIGS. 25 and 26. To facilitate comparison to FIG. 7, FIGS. 25 and 26 use reference numbers with primes for elements that are generally similar to elements identified by the corresponding unprimed reference numbers in FIG. 7. Each axial end portion of graft 430 includes a radially enlargeable connector structure 449. Connector structures 449 may have any of a large number of constructions. For example, each connector structure 449 may include one or more annularly compressible, serpentine-shaped, metal rings 448 (e.g., of nitinol). When such a ring is annularly compressed, the serpentine convolutions of the ring become more sharply curved and closer together. When such a ring is released to return to a more nearly relaxed state, the convolutions of the ring become somewhat straighter. If graft 450 is made of a metal (e.g., nitinol) framework 432 with a covering 434 (e.g., of silicone), rings 448 may be integral with framework 432, and covering 434 may continue into the vicinity of rings 448. Rings 448 may be formed to hold struts 436' substantially uniformly out against the inner surface of body tubing all the way around the circumference of the graft.

Figure 28:
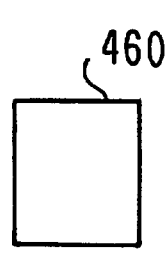
FIG. 28 is an elevational view of a structure that can be used to make a particular embodiment of the apparatus portion shown in FIG. 27.
Figure 29:
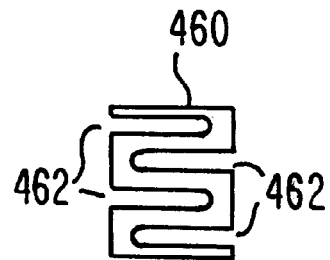
FIG. 29 is a simplified elevational view of a subsequent condition of the FIG. 28 structure during fabrication.

A particularly preferred way of producing a serpentine ring 448 is to start with a short length of thin-walled metal tubing 460 as shown in FIG. 28 and cut away interdigitated portions 462 from opposite axial ends of the tube as shown in FIG. 29. A typical thickness of tubing 460 is approximately 0.003 to 0.006 inches, and a typical width of metal left between adjacent slots 462 is about 0.008 inches. Slots 462 may be cut in tubing 460 using a laser. The structure shown in FIG. 29 is then radially enlarged and annealed. In its radially enlarged form, the structure has the general appearance shown in FIG. 27 when viewed from an axial end. Each point 458 is adjacent an axial end of the original tube 460. The structure can be resiliently radially compressed to the size of the original tube 460 or an even smaller size, and it will return to the radially enlarged size and shape whenever released from radial compression. Points 458 form radially outwardly extending high spots or raised portions that help ring 448 securely engage surrounding body tissue by locally projecting to a greater extent into the tissue, even though points 458 may not actually penetrate the tissue.

As an alternative or addition to reliance on a ring like 448 to resiliently (elastically) self-expand to the full circumferential size desired in a completed graft connection, some or all of the desired circumferential expansion of such a ring may be produced by inflating balloon 422' or using another selectively radially enlargeable structure inside the ring to plastically deform the ring.

Figure 29A:
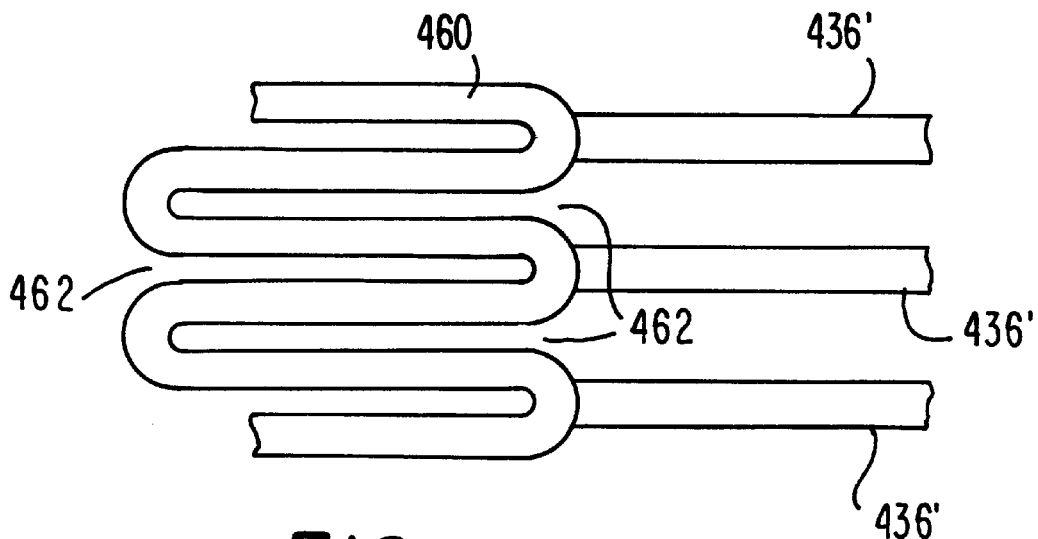
FIG. 29a is a simplified enlargement of a portion of FIG. 29 with other components added.

For use in a connector structure that includes struts like 436', each strut may be connected (e.g., welded) to a peak of the serpentine structure as shown for example in FIG. 29a. This may be done at any convenient time (e.g., before circumferential expansion of the FIG. 29 structure).

It will be noted that a ring 448 made as described above in connection with FIGS. 27–29a may be somewhat ribbon-like (e.g., because the width of the metal between slots 462 is greater than the thickness of that metal). Thus when the structure shown in FIG. 29 or 29a is circumferentially enlarged, the material in the peaks 458 of the convolutions tends to twist. This can give these peaks a shape which is especially effective in engaging adjacent body tissue. If struts like 436' are attached to these peaks as shown in FIG. 29a, the twisting of the peak material can be used to similarly twist the struts (e.g., to bias them in favor of radial outward projection and/or to rotate them about their longitudinal axes to properly orient hooks and/or barbs on them).

In the embodiment shown in FIGS. 25 and 26 struts 436' are connected to the distal end of the serpentine ring 448 of the connector 449, which is connected in turn to the distal end of frame 432'. Struts 436' are initially held in the form of a distally pointed cone by yieldable bands 437a, 437b, 437c, and 437d. As elsewhere along graft conduit 430', the spaces between struts 436' are substantially filled by a highly elastic material such as silicone rubber. Bands 437 may be made of a polymeric or other suitable yieldable material. Alternatively, bands 437 could be serpentine metal members that yield by becoming straighter. Bands 437 are initially strong enough to prevent struts 436' from flaring radially outward from conduit 430' as the struts are resiliently biased to do. However, bands 437 can be made to yield by inflating balloon 422' (on the distal end of tube 420') inside the annulus of struts 436'.

Struts 436' can be forced through tissue such as the wall of coronary artery 20 in their initial cone shape. Sufficient pushing force can be applied to the cone of struts 436' in any of several ways. For example, tube 420' may be metal (e.g., stainless steel) hypotube which can transmit pushing force to the cone of struts 436' by inflating balloon 422' to trap the base of the cone between balloon 422' and tube 440. Additional pushing force may then also be applied via tube 440 itself.

When a sufficient portion of the height of the cone of struts 436' is through the coronary artery wall, balloon 422' is inflated inside the cone as shown in FIG. 26 to cause bands 437 to yield. This allows struts 436' to flare radially outward inside the coronary artery, thereby anchoring the distal end of conduit 430' to the artery. Bands 437 may be made progressively weaker in the distal direction to facilitate prompt yielding of distal bands such as 437a and 437b in response to relatively little inflation of balloon 422', whereas more proximal bands such as 437c and 437d do not yield until somewhat later in response to greater inflation of balloon 422'. This progression of yielding may help ensure that the annulus of barbs flares out in the desired trumpet-bell shape inside the coronary artery.

Figure 26A:
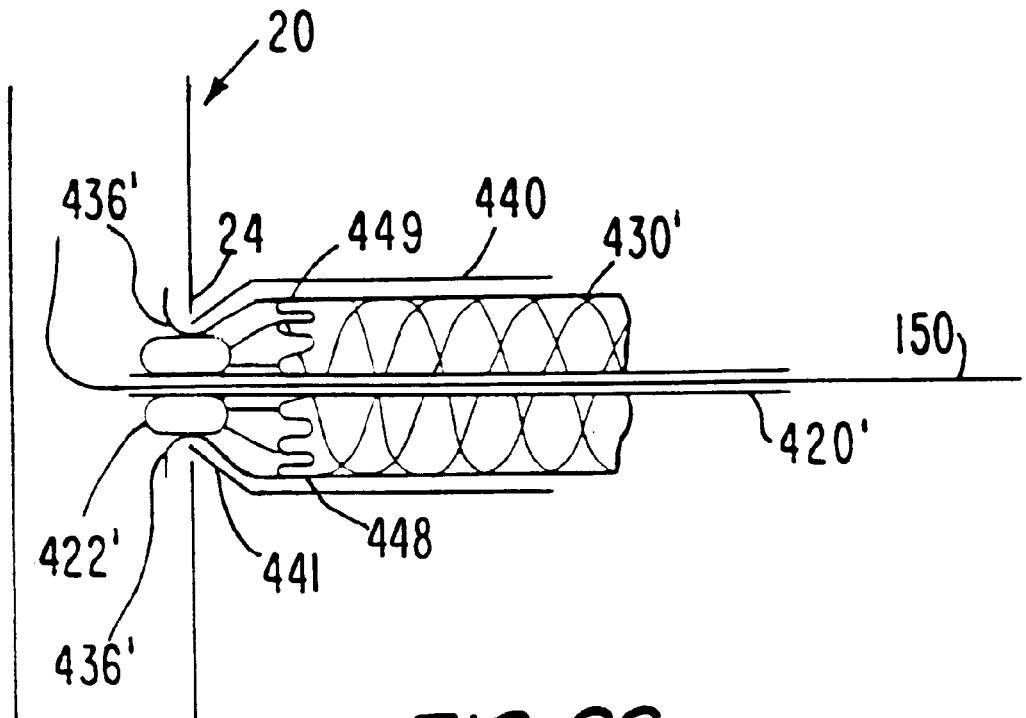
FIG. 26a is a simplified elevational view (partly in section) showing another possible alternative construction of portions of the FIG. 7 apparatus.

As shown in FIG. 26a, in another embodiment struts 436' are initially held in the form of a distally pointed cone by a yieldable cone 441 which is attached to or is part of tube 440. Cone 441 may be made of a polymeric or other suitable yieldable material. Cone 441 is initially strong enough to prevent struts 436' from flaring radially outward from conduit 430' as the struts 436' are resiliently biased to do. However, cone 441 can be made to yield by inflating balloon 422' (on the distal end of tube 420') inside the annulus of struts 436'. Struts 436' can be forced through tissue such as the wall of coronary artery 20 in their initial cone shape.

Sufficient pushing force can be applied to the cone of struts 436' in any of several ways. For example, tube 420' may be metal (e.g., stainless steel) hypotube which can transmit pushing force to the cone of struts 436' by inflating balloon 422' to trap the base of the cone between balloon 422' and tube 440. Additional pushing force may then also be applied via tube 440 itself.

When a sufficient portion of the height of the cone of struts 436' is through the coronary artery wall, balloon 422' is inflated inside the cone as shown in FIG. 26*a* to cause cone 441 to yield. This allows struts 436' to flare radially outward inside the coronary artery, thereby anchoring the distal end of conduit 430' to the artery. Cone 441 may be made progressively weaker in the distal direction to facilitate prompt yielding of distal end in response to relatively little inflation of balloon 422', whereas the more proximal end does not yield until somewhat later in response to greater inflation of balloon 422'. This progression of yielding may help ensure that the annulus of struts 436' flares out in the desired trumpet-bell shape inside the coronary artery. The cone 441 may be withdrawn with the tube 440, and may even be made part of tube 440.

Figure 26B:
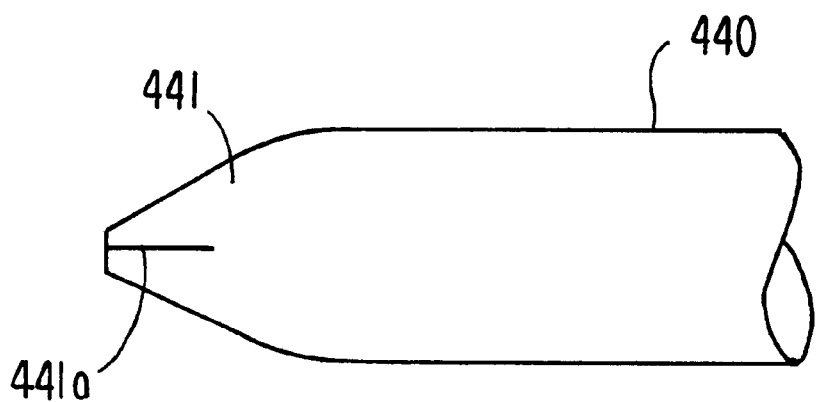
Figure 27:
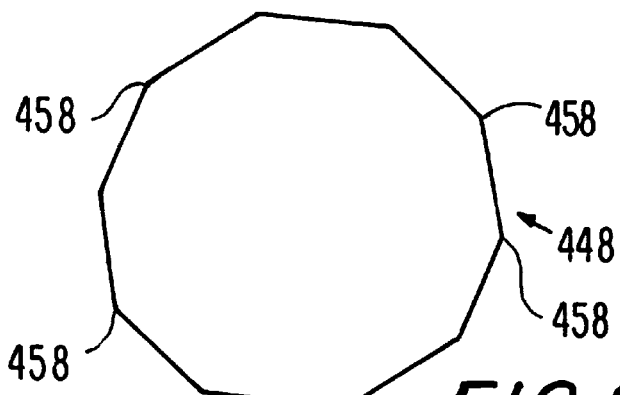
FIG. 27 is a simplified end view of an illustrative embodiment of a component of the graft shown in FIGS. 25 and 26.

FIG. 26*b* depicts tube 440 and cone 441 by themselves in order to better show that cone 441 may have a weakened zone 441*a* extending in the distal direction to help the cone yield to deploy struts 436' when balloon 422' is inflated. Weakened zone 441*a* can be a slit, a score line, a perforation line or any other generally similar structural feature.

Still another illustrative alternative embodiment of some of the instrumentation shown in FIG. 7 is shown in FIG. 30. To facilitate comparison to FIG. 7, FIG. 30 uses reference numbers with double primes for elements that are generally similar to elements identified by the corresponding unprimed reference numbers in FIG. 7. In the embodiment shown in FIG. 30, the distal end of artificial graft conduit 430" is attached to expandable ring 448. Elongated struts 436" extend distally from the distal end of ring 448. The distal ends of struts 436" are turned back in the proximal direction and extend just far enough into the distal end of tube 420" to be releasably retained by that tube. Struts 436" are resiliently biased to extend radially outward from ring 448, but are initially restrained from doing so by the presence of their distal end portions in the distal end of tube 420". Thus struts 436" initially form a distally pointing cone that can be pushed through tissue such as the wall of coronary artery 20 in the same manner that has been described above in connection with FIGS. 25 and 26. Structure 420", which may be metal (e.g., stainless steel) hypotube with an inflatable annular balloon 422" near its distal end, may be used to help push the cone through the tissue.

After the distal portion of the cone of struts 436" has been pushed through the wall of coronary artery 20, tube 420" is shifted proximally relative to the struts 436" to release the distal end portions of the barbs. This allows struts 436" to spring radially outward from ring 448 inside coronary artery 20, thereby anchoring the distal end of the graft conduit in the coronary artery. Ring 448 can then be circumferentially expanded to increase the size of the connection between coronary artery 20 and the distal portion of the graft conduit. If desired, each of struts 436" may be twisted 180° before it enters the distal end of tube 420". This promotes turning of the hook-like extreme distal end portions of the struts toward the coronary artery wall when the struts are released from tube 420".

Ring 448 and struts 436" may be made of any suitable material such as any 300-series stainless steel (e.g., 316L stainless steel). Another material that may be suitable for struts 436" is nitinol. As in previously described embodiments, the elastic cover 434 that forms part of conduit 430" preferably extends to regions 430*a* and 436".

In FIG. 30, the struts 436" are attached to ring 448 at the closest (distal-most) points of the ring 448. This causes the struts 436" to pull in the proximal direction when the ring 448 is expanded by balloon 422". This causes the hooks on the ends of the struts to pull into the surrounding tissue for a more secure attachment. The hooks on the ends of struts 436" may also have barbs formed thereon for an even more secure attachment to body tissue.

Figure 30A:
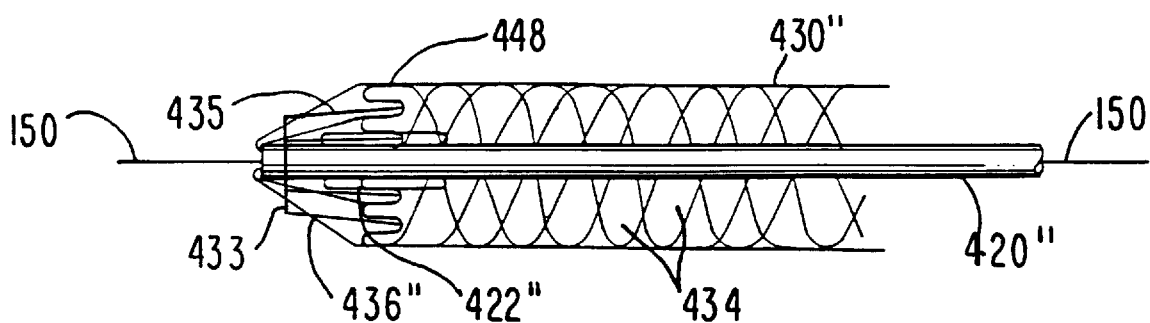
FIG. 30a is a simplified longitudinal sectional view showing still another possible alternative construction of portions of the apparatus shown in FIG. 7.

As shown in FIG. 30*a*, there may also be outer struts 435 which are attached to the farthest (proximal-most) points of the ring 448 and to a band 433 at their distal ends. When the ring 448 expands, the outer struts 435 are pushed in the distal direction, which causes band 433 to move distally, and therefore closer to the artery wall to help seal against the artery wall. In other words, the body tissue is trapped between radially outwardly extending struts 436" on the inside of the tissue wall and band 433 on the outside of the tissue wall. Circumferential expansion of ring 448 and consequent proximal motion of barbs 436" and distal motion of band 433 apply compressive stress to the tissue wall between those inner and outer portions of the connector.

Figure 31:
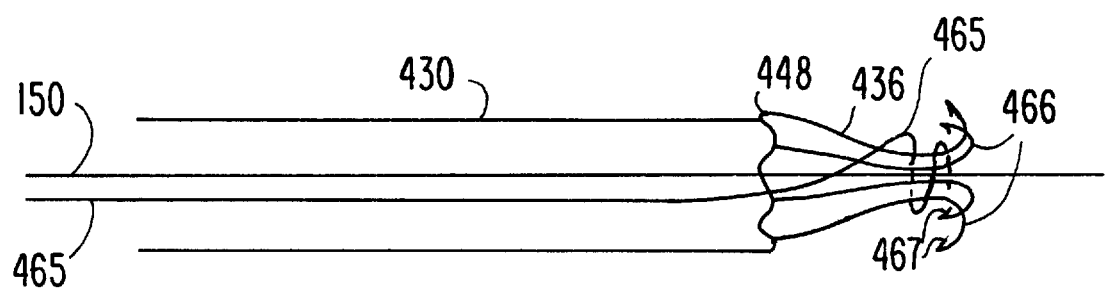
FIG. 31 is a simplified longitudinal sectional view showing yet another possible alternative construction of portions of the apparatus shown in FIG. 7.

Still another illustrative alternative embodiment of some of the instrumentation shown in FIG. 7 is shown in FIG. 31. In the embodiment shown in FIG. 31, the distal end of artificial graft conduit 430 is attached to expandable ring 448. Elongated struts 436 extend distally from the distal end of ring 448. The distal ends of struts 436 have hooks 466 having small barbs 467 at the ends. The struts 436 are turned back in the proximal direction. Struts 436 are resiliently biased to extend radially outward from ring 448, but they are initially restrained from doing so by the presence of their distal end portions wrapped by a restraining wire 465. Thus struts 436 initially form a distally pointing cone that can be pushed through tissue such as the wall of coronary artery 20 in the same manner that has been described above. The wire 465, which may be metal (e.g., stainless steel), is then pulled back proximally to unwrap the distal portion from around the struts. This allows struts 436 to spring radially outwardly from ring 448 inside coronary artery 20, thereby anchoring the distal end of the graft conduit in the coronary artery using the hooks 466 and barbs 467. Ring 448 can be circumferentially expanded at any suitable time to increase the size of the connection between coronary artery 20 and the distal portion of the graft conduit 430.

FIG. 32 shows a variation of the FIG. 31 apparatus. In the FIG. 32 variation, struts 436" are initially restrained by a loop or coil on the distal end of wire 465". Wire 465" extends distally from a lumen in the wall of tube 420. When it is desired to release struts 436" to extend radially outwardly, tube 420 is rotated about its central longitudinal axis. This rotates the loop or coil in wire 465", thereby releasing struts 436" one after another. After all of struts 436" have been released from the wire loop, wire 465" may be proximally retracted relative to tube 420 so that the loop in wire 465" is adjacent the distal end of that tube. Alternatively, wire 465" may be proximally retracted all the way into the lumen in the wall of tube 420 from which the wire initially extends.

Figure 33:
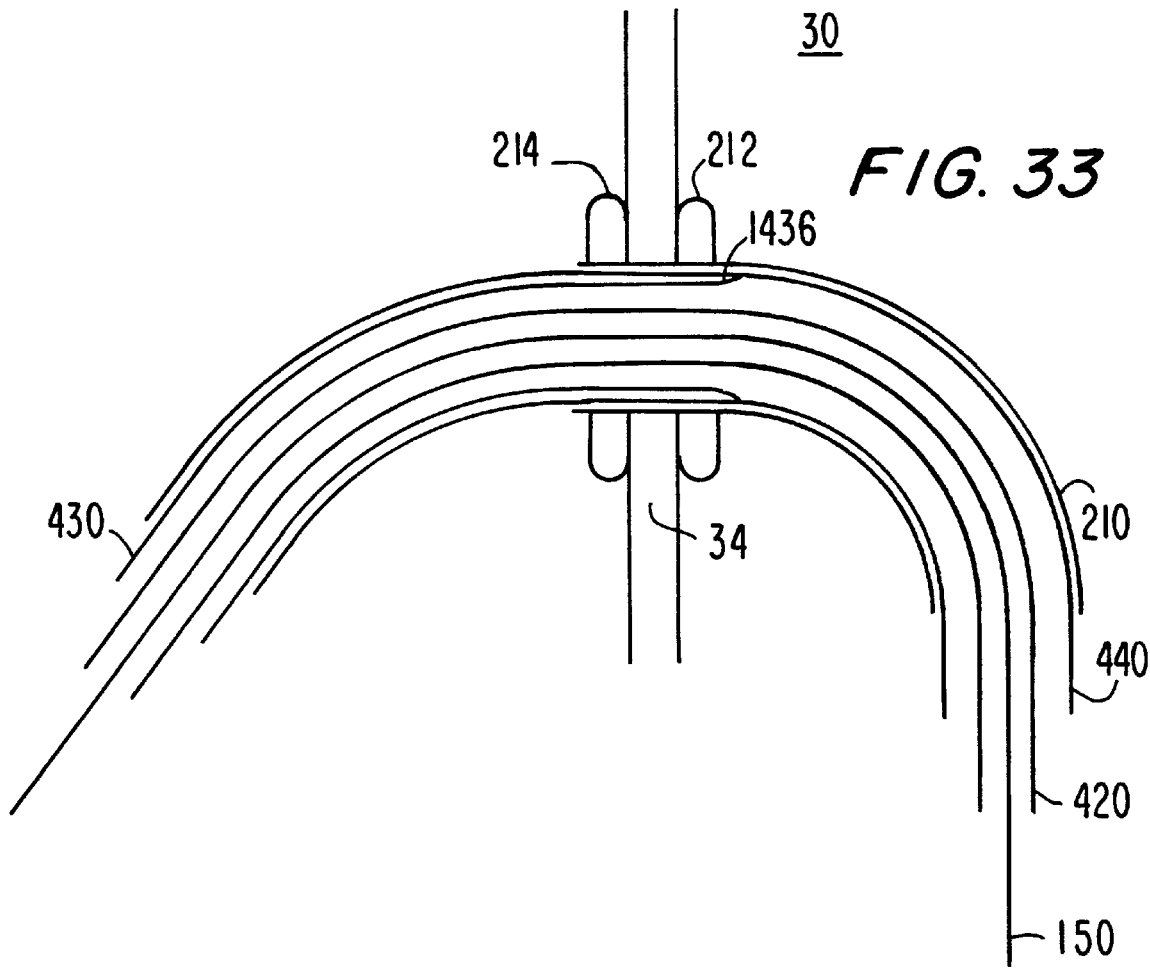
FIG. 33 is a view similar to FIG. 13 showing an alternative illustrative embodiment of certain components.

An alternative construction of the proximal end of artificial graft conduit 430 is shown in FIG. 33. The embodiment shown in FIG. 33 can be used with any construction of the distal end of conduit 430, but FIG. 33 assumes that the depicted proximal end construction is used with a distal end construction of any of the types shown in FIGS. 25–26a and 30–32.

In the embodiment shown in FIG. 33 the proximal end of conduit 430 has a plurality of struts 1436 that are resiliently biased to extend radially out from the remainder of the conduit. Initially, however, struts 1436 are confined within delivery tube 440 as shown in FIG. 33. Like distal struts 436, struts 1436 may be proximal extensions of the frame 432 of conduit 430, or they may extend proximally from a ring at or near the proximal end of conduit 430. This proximal ring may be similar to distal ring 448 described above in connection with FIGS. like FIG. 25. The covering 434 of conduit 430 may extend to all, part, or none of the length of struts 1436. Struts 1436 may include resilient hooks, and the free end portions of struts 1436 or the hooks on those struts may include barbs. Representative struts 1436, each with a hook 1466 and a barb 1467, are shown after deployment and in more detail in FIG. 34. This FIG. shows that struts 1436 flare out inside aorta 30 and that the free ends of hooks 1466 penetrate the aorta wall tissue shown at 34. Barbs 1467 engage the tissue like fish hook barbs to resist any tendency of hooks 1466 to pull out of the tissue.

Figure 34:
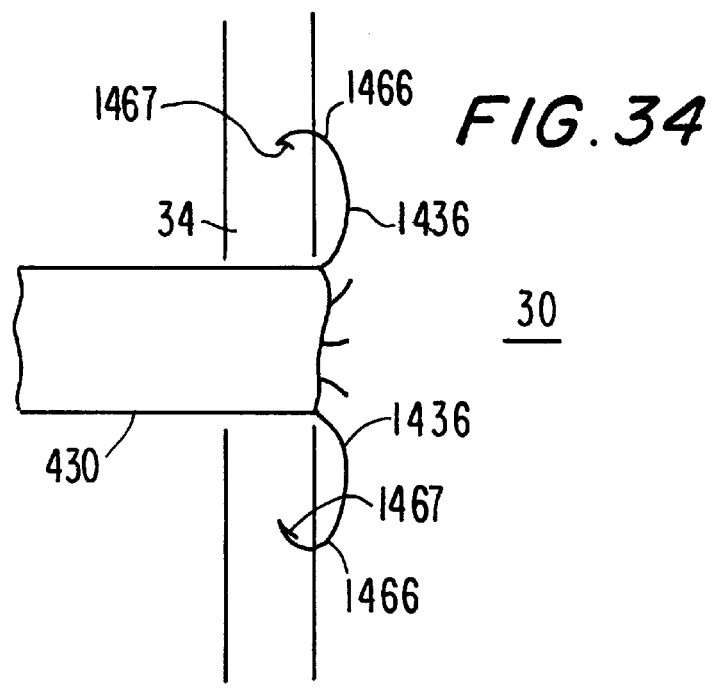
FIG. 34 is a view similar to a portion of FIG. 16 for the alternative embodiment shown in FIG. 33.

The proximal end of conduit 430 is attached to the wall of aorta 30 (after attachment of the distal end to coronary artery 20 as described above in connection with numerous other FIGS.) by proximally retracting delivery tube 440 so that struts 1436 can spring out against the inside of catheter 210 in the vicinity of proximal balloon 212. Then distal balloon 214 is deflated and catheter 210 is retracted proximally so that struts 1436 can spring out against the inside surface of the wall of aorta 30 as is generally shown in FIG. 34. If provided, hooks 1466 and barbs 1467 penetrate the aorta tissue as shown in FIG. 34.

As part of the procedure for connecting the proximal end of conduit 430 to the aorta, it may be desirable to proximally retract the balloon 422/422'/422" (described above in connection with numerous other FIGS.) to the proximal end of conduit 430 and to there re-inflate the balloon to help hold conduit 430 in place before proximally retracting delivery tube 440. The balloon can be deflated again at any suitable time (e.g., after delivery tube 440 has been proximally retracted). Balloon 422/422'/422" may additionally or alternatively be inflated during proximal retraction of catheter 210. This may help ensure that struts 1436 are fully and properly deployed and that the connection of conduit 430 to aorta 30 is properly molded. If a ring similar to ring 448 is part of the proximal conduit connection, inflation of balloon 422/422'/422" may be used to circumferentially expand that ring as part of the process of connecting conduit 430 to the aorta.

Figure 34A:
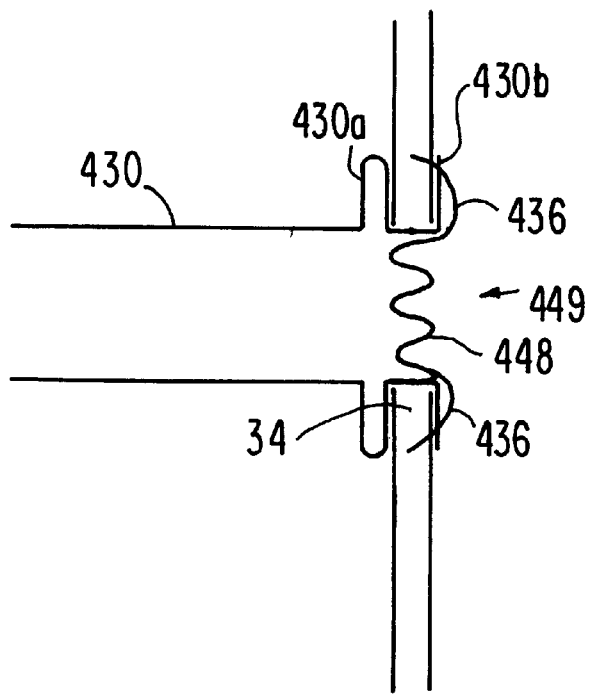
FIG. 34a is another view similar to FIG. 34 showing another alternative illustrative embodiment of the invention.
Figure 34B:
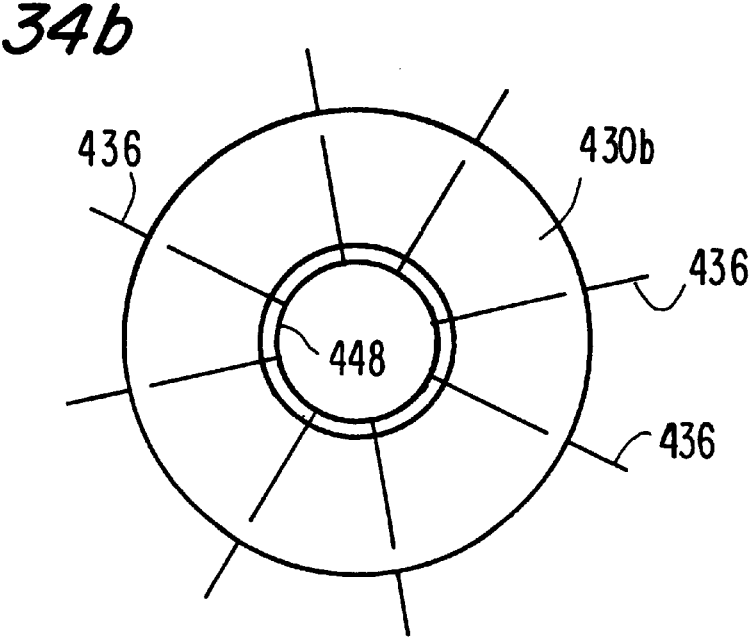

Possible refinements of a proximal connector of the general type shown in FIGS. 33 and 34 are shown in FIGS. 34a and 34b. (The structure shown in FIGS. 34a and 34b can also be used as a distal connector.) FIGS. 34a and 34b show the connector fully installed though an aperture in body tissue wall 34. Artificial graft conduit 430 is formed so that its proximal portion is resiliently biased to assume the shape shown in FIGS. 34a and 34b. In particular, this shape includes a medial, radially outwardly projecting, annular flange 430a, and a proximal, radially outwardly projecting, annular flap 430b. Flange 430a is intended to be deployed outside body tissue wall 34 as shown in FIG. 34a, while flap 34b is intended to be deployed inside the body tissue wall. In addition, a connector 449 (similar to the connectors 449 in earlier-described FIGS. such as FIGS. 25–30, 31, and 32) is provided adjacent flap 430b. Connector 449 includes a radially expandable serpentine ring 448 and a plurality of struts 436 which are resiliently biased to project radially outwardly. In this embodiment struts 436 pass through the structure of flap 430b to help push the flap up inside and against the inner surface of tissue wall 34.

As in previous embodiments, the structure shown in FIGS. 34a and 34b may be delivered to the intended location in the body inside a delivery tube (e.g., like tube 440 in FIG. 33). While the structure is inside the delivery tube, all of elements 430a, 430b, and 436 are constrained by that tube into a substantially tubular shape. When the delivery tube is proximally retracted from conduit 430, elements 430a, 430b, and 436 resiliently return to the shapes shown in FIGS. 34a and 34b, thereby making a secure and fluid-tight connection between the proximal end of conduit 430 and body tissue wall 34.

FIG. 35 illustrates another possible use of the connecting structures as described above, as well as illustrating other possible aspects of the invention. FIG. 35 illustrates a structure that can be used to deliver an artificial graft conduit, or a natural graft conduit, or both an artificial graft conduit and a natural graft conduit simultaneously (e.g., with the natural conduit coaxially inside the artificial conduit). In the particular case shown in FIG. 35 it is assumed that only natural graft conduit is being delivered, but it will be readily apparent that artificial graft conduit could be substituted for or added outside the natural graft conduit.

In the embodiment shown in FIG. 35 the cone of struts 436' is attached to the distal end of a natural graft conduit 530. The proximal end of natural graft conduit 530 is attached to ring 461. The cone of struts 436' is provided with relatively short, radially outwardly projecting prongs 433. Prongs 433 extend into and/or through the distal portion of the length of graft tubing 530, which (as has been mentioned) is assumed in this case to be natural body organ tubing such as saphenous vein. Ring 461 is similarly provided with radially outwardly extending prongs 462, which extend into and/or through the proximal portion of graft conduit 530. Ring 461 also includes resilient radially outwardly extending annular flaps 438a and 438b with prongs 439, all similar to correspondingly numbered elements in FIG. 8. Structure 420' is disposed around wire 150 inside structures 436', 450, 460, and 530. Delivery tube 440 is disposed around conduit 530.

The embodiment shown in FIG. 35 illustrates a structure which can be used to deliver and install natural body organ conduit without any full length artificial graft conduit being used. In a manner similar to what is shown in the previous FIGS., the structure shown in FIG. 35 is delivered to the operative site via wire 150. The cone of struts 436' is forced through the wall of coronary artery 20 and then flared radially outward inside the coronary artery to anchor the distal end of the graft conduit to that artery. The distal end of delivery tube 440 is pulled back as needed to aid in attachment of the distal end of the graft structure. Attachment of the proximal end of the graft structure to the wall of aorta 30 is performed similarly to what is shown in the above FIGS. Accordingly, with distal flap 438a just outside the wall of aorta 30, delivery tube 440 is pulled back proximally to expose that flap. Flap 438a is thereby released to spring out and engage the outer surface of the aorta wall. After that has occurred, proximal flap 438b is adjacent the inner surface of the aorta wall. Tube 440 is pulled back proximally even farther to expose flap 438b so that it can spring out and engage the inner surface of the aorta wall. Natural body organ graft 530 is now fully installed in the patient. Struts 436', 450, and 460 remain in place in the patient to help anchor the ends of graft conduit 530 and to help hold open the medial portion of that conduit.

FIG. 36 shows an alternative to what is shown in FIG. 35. In FIG. 36 a distal annular connector structure 449a is annularly attached to the distal end of conduit 530 (similar to conduit 530 in FIG. 35), and a proximal annular connector structure 449b is annularly attached to the proximal end of conduit 530. For example, each of connectors 449 may be sutured to the respective end of conduit 530. In that case connectors 449 may be inside or outside conduit 530. Each of connectors 449 may be similar to the connectors 449 in earlier-described FIGS. such as FIGS. 25–30, 31, and 32. Thus, each of connectors 449 includes a serpentine ring 448 with a plurality of struts 436 extending from the ring. With this construction, as an addition or alternative to suturing each connector 449 to conduit 530, the ring 448 of each connector may be inside the conduit and the high spots 458 (FIG. 27) on the ring may be used to dig into the tissue of conduit 530 (without actually penetrating the tissue) to secure or help secure the connector to the tissue.

The struts 436a of distal connector 449a extend in the distal direction from ring 448a and are initially restrained into a cone shape by a release wire 465 as shown in FIG. 31. The struts 436b of proximal connector 449b extend in the proximal direction from ring 448b and are initially constrained by being inside delivery tube 440. The struts 436a of distal connector 448a are deployed to spring radially outwardly and engage body tissue by proximally retracting release wire 465. The struts 436b of proximal connector 448b are deployed to spring radially outwardly and engage body tissue by proximally retracting delivery tube 440. The structure shown in FIG. 36 can be used in any of the ways that are described above for the structure shown in FIG. 35.

Figure 37:
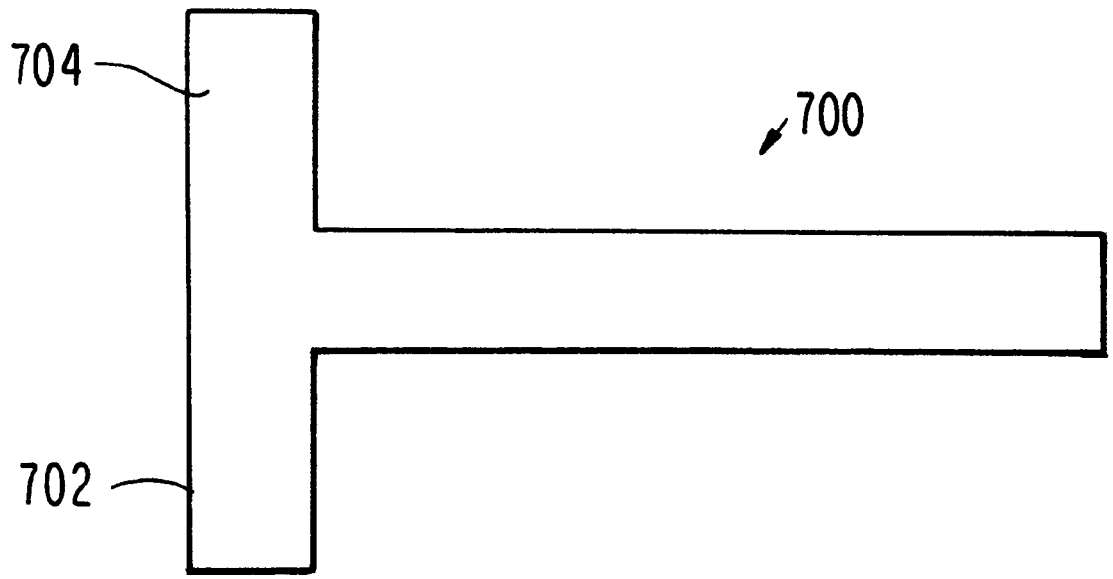
FIG. 37 is a simplified elevational view showing another illustrative embodiment of an artificial graft constructed in accordance with the invention.
Figure 38:
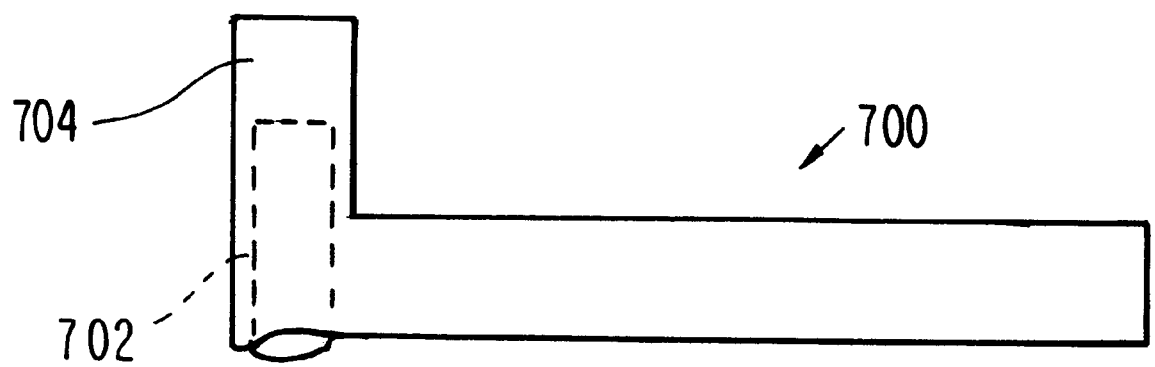
FIG. 38 is another view similar to FIG. 37 showing another operating condition of the FIG. 37 graft.
Figure 39:
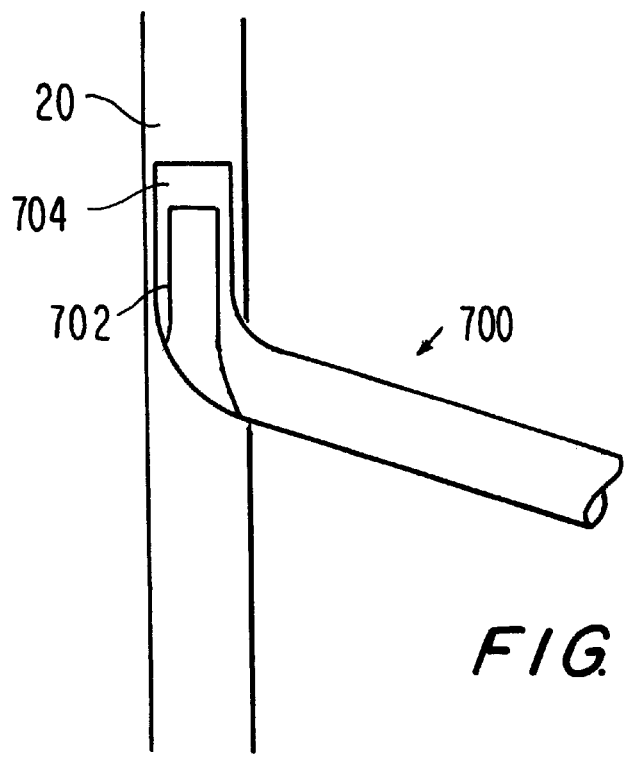
FIG. 39 is another view similar to FIG. 37 showing the graft being installed in tubular body tissue.
Figure 40:
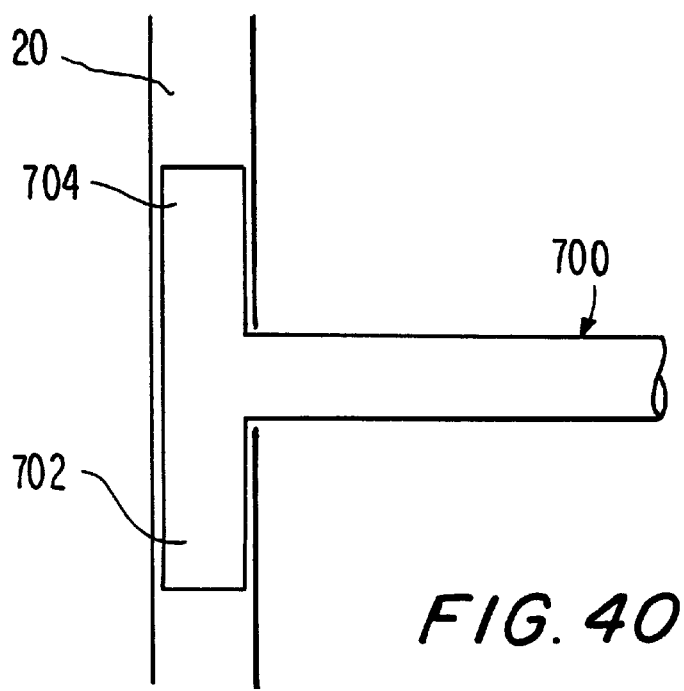
FIG. 40 is another view similar to FIG. 39 showing a later stage in the installation of the graft.

FIG. 37 shows a structure that may be used as an alternative to the embodiments described above. For example, structures like this may be used in place of the connectors using barbs, or wherever else a generally similar connecting structure is needed. A T-flange connector 700 is provided. It is constructed generally similar to the graft conduits 430 described above, having a frame, and a covering. The connector 700 is formed in the shape of a "T" of hollow tubular sections and is resiliently biased to return to this shape. The connector is initially deployed with one of the ends 702 of the top of the "T" inverted or compressed into the other end 704 of the top of the "T" as shown in FIG. 38. The compressed connector is then deployed using a tube 440 as described above. Once the tube 440 is withdrawn, the connector 700 expands to its original "T" shape. For example, the top of the "T" may be inserted into coronary artery 20 through an aperture in the side wall of that artery as shown in FIG. 39. After insertion, one leg 704 of the top of the "T" extends upstream along the coronary artery, and the other leg 702 extends downstream along that artery as shown in FIG. 40. The remainder of the "T" (i.e., the "vertical" portion of the "T") extends out of the aperture in the coronary artery so that the base of the "T" can be connected to the aorta (e.g., using any of the other connector structures and techniques described above). The fact that the top of the "T" extends both upstream and downstream along the coronary artery anchors the graft to the coronary artery.

As used herein, references to a patient's existing body organ tubing or the like include both natural and previously installed graft tubing (whether natural, artificial, or both). The artificial grafts of this invention may be coated (in the case of tubular grafts, on the inside and/or outside) to still further enhance their bio-utility. Examples of suitable coatings are medicated coatings, hydrophylic coatings, smoothing coatings, collagen coatings, human cell seeding coatings, etc. The above-described preferred porosity of the graft covering helps the graft to retain these coatings. Additional advantages of the artificial grafts of this invention are their elasticity and distensibility, their ability to be deployed through tubes of smaller diameter (after which they automatically return to their full diameter), the possibility of making them modular, their ability to accept natural body organ tubing concentrically inside themselves, their ability to support development of an endothelial layer, their compatibility with MRI procedures, their ability to be made fluoroscopically visible, etc.

It will be understood that the foregoing is only illustrative of the principles of the invention, and that various modifications can be made by those skilled in the art without departing from the scope and spirit of the invention. For example, the order of some steps in the procedures that have been described are not critical and can be changed if desired.

The invention claimed is:

1. A connector for use in connecting an axial end portion of a tubular medical graft to the side wall of a patient's tubular body tissue conduit so that the lumen of the graft communicates with the lumen of the conduit through an aperture in the side wall of the conduit to permit body fluid flow between the lumens without leakage of body fluid to the outside of the graft and the conduit adjacent the connector comprising:

an annular structure having first and second axially adjacent substructures, the first substructure being configured to be disposed substantially concentrically inside the axial end portion of the graft and being circumferentially enlargeable to press the axial end portion of the graft radially outwardly toward the body tissue surrounding the aperture, and the second substructure including a plurality of struts that are configured to extend substantially radially outwardly to engage the body tissue surrounding the aperture and hold the axial end portion of the graft in body-fluid-tight engagement with the side wall of the conduit annularly around the aperture wherein the first substructure is configured to circumferentially enlarge to at least some degree by plastic deformation of the first substructure.

2. The connector defined in claim 1 wherein the first substructure is resiliently biased to circumferentially enlarge to at least some degree by itself.

3. The connector defined in claim 1 wherein the annular structure further comprises:

a ring having convolutions that repeatedly traverse a circumference of the annular structure, the ring being circumferentially enlargeable by straightening out the convolutions to some degree.

4. The connector defined in claim 1 wherein the struts are configured to extend through the annular portion of the graft to engage surrounding body tissue.

5. The connector defined in claim 1 wherein the struts include hooks configured to penetrate surrounding body tissue.

6. The connector defined in claim 1 wherein the struts include barbs configured to penetrate surrounding body tissue and to resist withdrawal of the struts from the penetrated body tissue.

7. The connector defined in claim 1 wherein the struts are resiliently biased to extend substantially radially outwardly to engage surrounding body tissue, and wherein the struts are additionally configured to elastically deflect substantially parallel to an axis with which the annular structure is substantially coaxial.

8. The connector defined in claim 1 wherein the struts are resiliently biased to extend substantially radially outwardly to engage surrounding body tissue, and wherein the struts are additionally configured to elastically deflect substantially into a cone which has its apex on an axis about which the annular structure is substantially coaxial.

9. The connector defined in claim 1 wherein the annular structure is at least partly made of nitinol.

10. The connector defined in claim 1 wherein the annular structure is at least partly made of stainless steel.

11. The connector defined in claim 3 wherein the ring is produced from a tube by removing interdigitated portions from the tube, alternating removed portions extending in from opposite ends of the tube.

12. The connector defined in claim 11 wherein the tube has thickness less than the spacing between adjacent removed portions.

13. The connector defined in claim 1 wherein the annular structure further comprises:

a tissue clamping structure configured to move toward the struts in response to circumferential enlargement of the annular structure in order to clamp tissue between the clamping structure and the struts.

14. The connector defined in claim 13 wherein the annular structure further comprises:

a ring which is serpentine alone a circumference of the annular structure, the struts being connected to the ring adjacent one axial end of the connector and the tissue clamping structure being attached to the ring adjacent the other axial end of the connector so that when the ring is circumferentially enlarged and the ring accordingly becomes less serpentine, the struts and the tissue clamping structure move toward one another.

15. The connector defined in claim 14 wherein the tissue clamping structure comprises:

a second ring substantially parallel to and concentric with the first-mentioned ring.

16. The connector defined in claim 15 wherein the tissue clamping structure comprises a plurality of struts connecting the second ring to the first-mentioned ring adjacent said other axial end of the connector.

17. The connector defined in claim 7 further comprising:

a tubular structure axially reciprocable relative to the connector into and out of a position in which the tubular structure is substantially concentric outside the annular structure and releasably holds the struts substantially parallel to the axis with which the annular structure is substantially coaxial.

18. The connector defined in claim 8 further comprising:

a yieldable structure for releasably holding the struts in the cone.

19. The connector defined in claim 18 wherein the yieldable structure comprises:

a yieldable band around the struts.

20. The connector defined in claim 18 wherein the yieldable structure comprises:

a yieldable cone over the struts.

21. The connector defined in claim 8 further comprising:

a removable member around the struts.

22. The connector defined in claim 21 wherein the removable member comprises:

a wire wrapped around the struts.

23. The connector defined in claim 21 wherein the removable member comprises:

a coil around the struts configured to release the struts when the coil is rotated about its central longitudinal axis.

24. The connector defined in claim 8 wherein each of the struts includes an initially radially inwardly directed hook, and wherein the connector further comprises:

a removable member for releasably engaging the hooks.

25. The connector defined in claim 1 wherein the annular structure further comprises:

a multi-sided ring having a plurality of radially outwardly pointing corners circumferentially spaced from one another around the ring.

* * * * *